United States Patent [19]

Ogawa et al.

[11] Patent Number: 5,300,513
[45] Date of Patent: Apr. 5, 1994

[54] CARBOSTYRIL DERIVATIVES AND PHARMACEUTICAL COMPOSITION CONTAINING THE SAME

[75] Inventors: Hidenori Ogawa, Tokushima; Hisashi Miyamoto, Uji; Kazumi Kondo, Tokushima; Hiroshi Yamashita, Tokushima; Kenji Nakaya, Tokushima; Hajime Komatsu, Tokushima; Michinori Tanaka, Tokushima; Kazuyoshi Kitano, Tokushima; Takafumi Fujiioka, Tokushima; Shuji Teramoto, Tokushima; Michiaki Tominaga, Tokushima; Yoichi Yabuuchi, Tokushima, all of Japan

[73] Assignee: Otsuka Pharmaceutical Co., Ltd., Tokyo, Japan

[21] Appl. No.: 740,676

[22] Filed: Aug. 6, 1991

[30] Foreign Application Priority Data

Aug. 7, 1990 [JP] Japan ................... 2-210025

[51] Int. Cl.$^5$ .................... A61K 31/47; C07D 401/12
[52] U.S. Cl. .................... 514/312; 514/278; 544/58.6; 544/128; 544/237; 544/238; 544/284; 544/333; 544/353; 544/363; 546/16; 546/157; 546/158; 546/148
[58] Field of Search ............ 546/157, 158, 16; 514/312, 278

[56] References Cited

FOREIGN PATENT DOCUMENTS 0336629 5/1977 Austria .
0296560 12/1988 European Pat. Off. .
0382185 8/1990 European Pat. Off. .
2459089 6/1975 Fed. Rep. of Germany .

OTHER PUBLICATIONS

*Chemical Abstracts*, vol. 114, No. 1, Jan. 7, 1991 (Abstract No. 6 302u).
*Chemical Abstracts*, vol. 81, No. 13, Sep. 30, 1974 (Abstract No. 77 786r).

*Primary Examiner*—C. Warren Ivy
*Assistant Examiner*—James H. Turnipseed
*Attorney, Agent, or Firm*—Sughrue, Mion, Zinn, Macpeak & Seas

[57] ABSTRACT

Novel carbostyril derivatives of the formula:

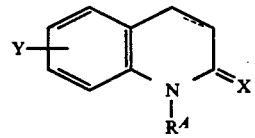

wherein X is O or S; Y is H or alkyl; $R^4$ is a group of the

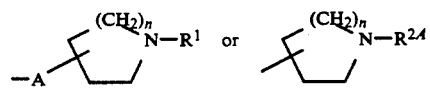

{wherein n is 1 or 2, A is alkylene, $R^1$ is benzoyl having optionally 1-3 substituents, $R^{24}$ is

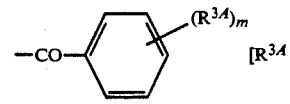

is (i) alkoxy, (ii) substituted or unsubstituted 5- or 6-membered heterocylic group, (iii) alkenylthio, (iv) pyrrolidinyl-alkyl—S—, (v) pyrrolidinyl-alkyl—SO—, (vi) pyrrolidinyl-alkyl—SO$_2$—, (vii) —O—B—NR$^4$R$^5$ [B is alkylene having optionally OH, R$^4$ is H, R$^5$ is tricyclo[3.3.1.1]decanyl, tricyclo[3.3.1.1]decanylalkyl, etc., or R$^4$ and R$^5$ may together form a group of

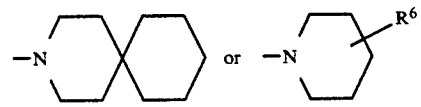

(R$^6$ is substituted or unsubstituted amino)] or (viii) sub- (Abstract continued on next page.)

stituted alkoxy; m is 1 to 3]}, which have excellent vasopressin antagonistic activities and are useful as vasodilator, hypotensive agent, water diuretics, platelet agglutination inhibitor, and a vasopressin antagonistic composition containing the compound as the active ingredient.

31 Claims, No Drawings

CARBOSTYRIL DERIVATIVES AND PHARMACEUTICAL COMPOSITION CONTAINING THE SAME

This invention relates to novel carbostyril derivatives which have excellent vasopressin antagonistic activities and are useful as vasodilator, hypotensive agent, water diuretics, platelet agglutination inhibitor, and a pharmaceutical composition containing said compound as the active ingredient. The carbostyril derivatives of this invention have the following formula:

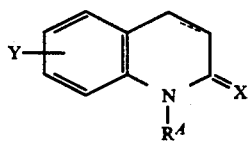
(1)

wherein X is oxygen atom or sulfur atom,
Y is hydrogen atom or a lower alkyl,
$R^4$ is a group of the formula:

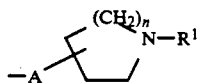

wherein n is 1 or 2, A is a lower alkylene, and $R^1$ is a benzoyl which phenyl ring may optionally have one to three substituents selected from a lower alkoxy and an amino having optionally a lower alkyl substituent, or $R^4$ is a group of the formula:

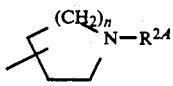

wherein n is as defined above, and $R^{2A}$ is a group of the formula:

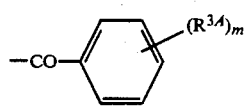

{wherein $R^{3A}$ is i) a lower alkoxy, ii) a 5- or 6-membered heterocylic group having 1 to 2 hetero atoms selected from nitrogen atom, oxygen atom and/or sulfur atom which may optionally have a substitutent selected from a lower alkyl, an oxo, a phenyl having optionally a substitutent selected from a halogen atom and a lower alkoxy on the phenyl ring, and a phenylthio having optionally a substitutent selected from nitro and amino, iii) a lower alkenylthio, iv) a pyrrolidinyl-substituted lower alkylthio, v) a pyrrolidinyl-substituted lower alkylsulfinyl, vi) a pyrrolidinyl-substituted lower alkylsulfonyl, vii) a group of the formula:

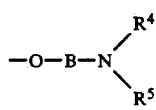

[wherein B is a lower alkylene having optionally a hydroxy substituent, $R^4$ is hydrogen atom and $R^5$ is tricyclo[3.3.1.1]decanyl, tricyclo[3.3.1.1]decanyl-lower alkyl, a halogen-substituted lower alkyl, a lower alkoxycarbonyl-lower alkanoyloxy-lower alkyl, a lower alkanoyl, or a lower alkenyl, or $R^4$ and $R^5$ may bind together with the nitrogen atom to which they bond to form a group of the formula:

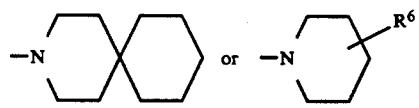

($R^6$ is an amino which may optionally be substituted by a lower alkanoyl having optionally one to three halogen substituents)], or viii) a lower alkoxy having two substituents selected from an aminocarbonyloxy having optionally a lower alkyl substituent and a group of the formula:

($R^7$ and $R^8$ are the same or different and are each hydrogen atom or a lower alkyl), m is an integer of 1 to 3}, the bond between 3- and 4-positions of the carbostyril ring is single bond or double bond, provided that when all of $R^{3A}$ are lower alkoxy or when $R^5$ is a lower alkanoyl, X is sulfur atom, and that when $R^5$ is a lower alkenyl and X is oxygen atom, B is a lower alkylene having a hydroxy substituent, and further that when $R^{3A}$ is a heterocyclic group having a lower alkyl or oxo substituent, the heterocyclic group is bound to the phenyl ring at the position other than the hetero atom.

The carbostyril derivatives of the present invention include also compounds of the following formula:

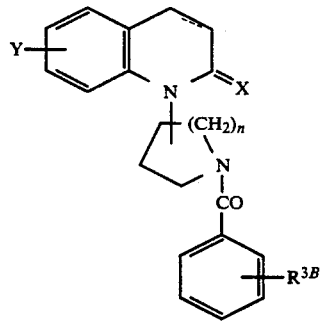
(1B)

wherein X, Y, n and the bond between 3- and 4-positions of the carbostyril ring are as defined above, $R^{3B}$ is a 7- to 10-membered monocyclic or dicyclic heterocyclic group having 1 to 2 hetero atoms selected from nitrogen atom, oxygen atom and/or sulfur atom which may optionally have a substitutent selected from a lower alkyl, an oxo, a phenyl having optionally a substitutent selected from a halogen atom and a lower alkoxy on the phenyl ring, and a phenylthio having optionally a substitutent selected from nitro and amino.

The carbostyril derivatives of the formulae (1) and (1B) and their salts have excellent vasopressin antagonistic activities and vasodilaring activity, hypotensive activity, activity for inhibiting saccharide release in liver, activity for inhibiting growth of mesangium cells, water diuretic activity, platelet agglutination inhibitory activity and are useful as vasodilator, hypotensive agent, water diuretics, platelet agglutination inhibitor and are used for the prophylaxis and treatment of hypertension, edema, ascites, heart failure, renal function disorder, vasopressin parasecretion syndrome (SIADH), hepatocirrhosis, hyponatremia, hypokaliemia, diabetic, circulation disorder, and the like.

Each group in the above formulae (1) and (IB) includes specifically the following groups.

The "lower alkoxy" includes a straight chain or branched chain alkoxy group having 1 to 6 carbonatoms, for example, methoxy, ethoxy, propoxy, isopropoxy, butoxy, tert-butoxy, pentyloxy, hexyloxy, and the like.

The "lower alkyl" includes a straight chain or branched chain alkyl group having 1 to 6 carbon atoms, for example, methyl, ethyl, propyl, isopropyl, butyl, tert-butyl, pentyl, hexyl, and the like.

The "lower alkylene" includes a straight chain or branched chain alkylene group having 1 to 6 carbon atoms, for example, methylene, ethylene, trimethylene, 2-methyltrimethylene, 2,2-dimethyltrimethylene, 1-methyltrimethylene, methylmethylene, ethylmethylene, tetramethylene, pentamethylene, hexamethylene, and the like.

The "lower alkanoyl" includes a straight chain or branched chain alkanoyl group having 1 to 6 carbon atoms, for example, formyl, acetyl, propionyl, butyryl, isobutyryl, pentanoyl, tert-butylcarbonyl, hexanolyl, and the like.

The "amino having optionally a lower alkyl substituent" includes an amino optionally having one or two substituents of a straight chain or branched chain alkyl group having 1 to 6 carbon atoms, for example, amino, methylamino, ethylamino, propylamino, isopropylamino, butylamino, tert-butylamino, pentylamino, hexylamino, dimethylamino, diethylamino, dipropylamino, dibutylamino, dipentylamino, dihexylamino, N-methyl-N-ethylamino, N-ethyl-N-propylamino, N-methyl-N-butylamino, N-methyl-N-hexylamino, and the like.

The "benzoyl which phenyl ring may optionally have one to three substituents selected from a lower alkoxy and an amino having optionally a lower alkyl substituent" includes a benzoyl group which phenyl ring may optionally have one to three substituents selected from a straight chain or branched chain alkoxy group having 1 to 6 carbon atoms and an amino having optionally one or two substituents of a straight chain or branched chain alkyl group having 1 to 6 carbon atoms, for example, benzoyl, 2-aminobenzoyl, 4-aminobenzoyl, 4-methylaminobenzoyl, 3-ethylaminobenzoyl, 2-(N-methyl-N-ethylamino)benzoyl, 3-(N-methyl-N-hexylamino)-benzoyl, 4-dimethylaminobenzoyl, 4-dipentylaminobenzoyl, 2-isopropylaminobenzoyl, 3-butylaminobenzoyl, 4-(N-methyl-N-ethylamino)benzoyl, 2,3-bis(dimethylamino)benzoyl, 3,4-bis(methylamino)benzoyl, 3,4,5-tri(methylamino)benzoyl, 2,6-di(N-methyl-N-ethylamino)benzoyl, 2-methoxybenzoyl, 3-methoxybenzoyl, 4-methoxybenzoyl, 2-ethoxybenzoyl, 3-ethoxybenzoyl, 4-ethoxybenzoyl, 4-isopropoxybenzoyl, 3-butoxybenozyl, 4-pentyloxybenzoyl, 4-hexyloxybenzoyl, 3,4-dimethoxybenzoyl, 3-ethoxy-4-methoxybenzoyl, 2,3-dimethoxybenzoyl, 2,4-dimethoxybenzoyl, 3,4-diethoxybenzoyl, 2,4-diethoxybenzoyl, 2,5-dimethoxybenzoyl, 2,6-dimethoxybenzoyl, 3,5-dimethoxybenzoyl, 3,4-dipentyloxybenzoyl, 3,4,5-trimethoxybenozyl, 2-methoxy-4-dimethylaminobenzoyl, and the like.

The "lower alkylene having optionally a hydroxy substituent: includes a straight chain or branched chain alkylene group having 1 to 6 carbon atoms which has optionally a hydroxy substituent, for example, 2-hydroxytrimethylene, 2-hydroxytetramethylene, 2,3-cinydroxytetramethylene, 3-hydroxypentamethylene, 3-hydroxytetramethylene, 5-hydroxyhexamethylene, and the like.

The "tricyclo[3.3.1.1]decanyl-substituted lower alkyl" includes a tricyclo[3.3.1.1]decanyl-substituted straight chain or branched chain alkyl group having 1 to 6 carbon atoms, for example, tricyclo[3.3.1.1]decanylmethyl, 2-tricyclo[3.3.1.1]decanylethyl, 1-tricyclo[3.3.1.1]decanylethyl, 3-tricyclo[3.3.1.1]decanylpropyl, 4-tricyclo[3.3.1.1]decanylbutyl, 5-tricyclo[3.3.1.1]decanylpentyl, 6-tricyclo[3.3.1.1]decanylhexyl, 1,1-dimethyl-2-tricyclo[3.3.1.1]decanylethyl, 2-methyl-3-tricyclo[3.3.1.1]decanylpropyl, and the like.

The "halogen-substituted lower alkyl" includes a straight chain or branched chain alkyl group having 1 to 6 carbon atoms which has one to three halogen substituents, for example, trifluoromethyl, trichloromethyl, chloromethyl, bromomethyl, fluoromethyl, iodomethyl, difluoromethyl, dibromomethyl, 2-chloroethyl, 2,2,2-trifluoroethyl, 2,2,2-trichloroethyl, 3-chloropropyl, 2,3-dichloropropyl, 4,4,4-trichlorobutyl, 4-fluorobutyl, 5-chloropentyl, 3-chloro-2-methylpropyl, 5-bromohexyl, 5,6-dichlorohexyl, and the like.

The "lower alkoxycarbonyl-lower alkanoyloxy-lower alkyl" includes an alkoxycarbonyl-alkanoyloxy-alkyl group wherein the alkoxycarbonyl moiety is a straight chain or branched chain alkoxycarbonyl group having 1 to 6 carbon atoms and the alkanoyloxy moiety is a straight chain or branched chain alkanoyloxy group having 2 to 6 carbon atoms, and the alkyl moiety is a straight chain or branched chain alkyl group having 1 to 6 carbon atoms, for example, (2-methoxycarbonylacetyloxy)methyl, 2-(2-ethoxycarbonyl acetyloxy)ethyl, 3-(3-propoxycarbonylpropionyloxy)propyl, 4-(4-butoxycarbonylbutyryloxy)butyl, 5-(5-pentyloxycarbonylpentanoyloxy)pentyl, 6-(6-tert-butyloxycarbonylhexanoyloxy)-hexyl, 1,1-dimethyl-2-(2-hexyloxycarbonylacetyloxy)ethyl, 2-methyl-3-(3-ethoxycarbonylpropionyloxy)propyl, and the like.

The "lower alkenyl" includes a straight chain or branched chain alkenyl group having 2 to 6 carbon atoms, for example, vinyl, allyl, 2-butenyl, 3-butenyl, 1-methylallyl, 2-pentenyl, 2-hexenyl, and the like.

The "lower alkanoyl which may optionally have one to three halogen substituents" includes a straight chain or branched chain alkanoyl group having 1 to 6 carbon atoms which may optionally have one to three substituents of a halogen atom, for example, formyl, acetyl, propionyl, butyryl, isobutyryl, pentanoyl, tert-butylcarbonyl, hexanoyl, 2,2,2-trifluoroacetyl, 2,2,2-trichloroacetyl, 2-chloroacetyl, 2-bromoacetyl, 2-fluoroacetyl, 2-iodoacetyl, 2,2-difluoroacetyl, 2,2-dibromoacetyl, 3,3,3-trifluoropropionyl, 3,3,3-trichloropropionyl, 3-chloropropionyl, 2,3-dichloropropionyl, 4,4,4-trichlorobutyryl, 4-fluorobutyryl, 5-chloropentanoyl, 3-chloro-2-methylpropionyl, 6-bromohexanoyl, 5,6-dibromohexanoyl, and the like.

The "aminocarbonyloxy having optionally a lower alkyl substituent" includes an aminocarbonyloxy having optionally one to two substituents of a straight chain or branched chain alkyl group having 1 to 6 carbon atoms, for example, aminocarbonyloxy, methylaminocarbonyloxy, ethylaminocarbonyloxy, propylaminocarbonyloxy, isopropylaminocarbonyloxy, butylaminocarbonyloxy, tert-butylaminocarbonyloxy, pentylaminocarbonyloxy, hexylaminocarbonyloxy, dimethylaminocarbonyloxy, diethylaminocarbonyloxy, dipropylaminocarbonyloxy, dibutylaminocarbonyloxy, dipentylaminocarbonyloxy, dihexylaminocarbonyloxy, N-methyl-N-ethylaminocarbonyloxy, N-ethyl-N-propylaminocarbonyloxy, N-methyl-N-butylaminocarbonyloxy, N-methyl-N-hexylaminocarbonyloxy, and the like.

The "lower alkoxy having two substituents selected from an aminocarbonyloxy having optionally a lower alkyl substituent and a group of the formula: —$NR^7R^8$ ($R^7$ and $R^8$ are the same or different and are each hydrogen atom or a lower alkyl)" includes a straight chain or branched chain alkoxy group having 1 to 6 carbon atoms which has two substituents selected from an aminocarbonyloxy having one to two substituents of a straight chain or branched chain alkyl group having 1 to 6 carbon atoms and a group of the formula: —$NR^7R^8$ ($R^7$ and $R^8$ are the same or different and are each hydrogen atom or a straight chain or branched chain alkyl group having 1 to 6 carbon atoms), for example, 5-methylaminocarbonyloxy-6-diethylaminohexyloxy, 2-ethylaminocarbonyloxy-3-dimethylaminopropoxy, 3-propylaminocarbonyloxy-4-methylaminobutoxy, 5-butylaminocarbonyloxy-6-propylaminohexyloxy, 3-pentylaminocarbonyloxy-4-pentylaminobutoxy, 4-hexylaminocarbonyloxy-5-hexylaminopentyloxy, 1-(N-methyl-N-ethylaminocarbonyloxy)-2-diethylaminoethoxy, 5-methylaminocarbonyloxy-6-(N-methyl-N-ethylamino)hexyloxy, and the like.

The "5- or 6-membered, or 7- to 10-membered monocyclic or dicyclic heterocyclic group having 1 to 2 hetero atoms selected from nitrogen atom, oxygen atom and/or sulfur atom" includes, for example, pyrrolidinyl, piperidinyl, piperazinyl, morpholinyl, thiomorpholinyl, tetrahydrofuryl, thienyl, pyrrolyl, furyl, pyrazolyl, pyridyl, pyridazinyl, thiazolyl, oxazolyl, imidazolyl, pyrimidyl, pyrazyl, quinolyl, benzimidazolyl, indolyl, isoindolyl, cinnolyl, quinoxalyl, phthalazinyl, quinazolyl, benzo[b]furyl, benzo[b]thienyl, and the like.

The above "heterocyclic group which may optionally have a substituent selected from a lower alkyl, an oxo, a phenyl having optionally a substituent selected from a halogen atom and a lower alkoxy on the phenyl ring, and a phenylthio having optionally a substituent selected from nitro and amino" includes the above-mentioned heterocyclic groups which may optionally have one to three substituents selected from a straight chain or branched chain alkyl group having 1 to 6 carbon atoms, an oxo, a phenyl having optionally one to three substituents selected from a halogen atom and a straight chain or branched chain alkoxy group having 1 to 6 carbon atoms on the phenyl ring, and a phenylthio group having optionally one to three substituents selected from nitro and amino on the phenyl ring, for example, 2-ethyl-1-imidazolyl, 2-ethyl-4-methyl-1-imidazolyl, 3-methylpyrazolyl, 3,5-dimethylpyrazolyl, 1-methyl-2-imidazolyl, 1-oxothiomorpholino, 1,1-dioxothiomorpholino, 2-phenyl-1-imidazolyl, 3-phenyl-1-imidazolyl, 2-(2-nitrophenylthio)-1-imidazolyl, 2-(4-chlorophenyl)-1-imidazolyl, 2-(4-methoxyphenyl)-1imidazolyl, 2-(2-aminophenylthio)-1-imidazolyl, 2-phenylthio-1-imidazolyl, 2-propyl-1-pyrrolidinyl, 3-butyl-2pyrrolidinyl, 4-pentyl-1-piperidinyl, 1-hexyl-4-piperidinyl, 4-methyl-1-piperazinyl, 3,5-dimethyl-1-piperazinyl, 4-ethyl2-piperazinyl, 2-methyl-4-morpholino, 3-ethyl-2-morpholinyl, 4-propyl-3-piperazinyl, 4-butyl-3-morpholinyl, 2-methyl-3thiomorpholinyl, 3-ethyl-2-thiomorpholinyl, 3-pentyl-1thiomorpholino, 4-hexyl-2-thiomorpholinyl, 3-methyl-2tetrahydrofuryl, 2-methyl-3-thienyl, 1-methyl-3-pyrrolyl, 3-ethyl-1-pyrrolyl, 1-propyl-2-pyrrolyl, 3-methyl-2-furyl, 3-methyl-4-pyrazolyl, 4-methyl-1-pyrazolyl, 2-methyl-3pyridyl, 3-ethyl-2-pyridyl, 2-methyl-4-pyridyl, 3-methyl-4-pyridazinyl, 2-methyl-4-thiazolyl, 2-ethyl-5-oxazolyl, 1,2,4-trimethyl-5-imidazolyl, 4-propyl-2-imidazolyl, 5-butyl-4-imidazolyl, 4-pentyl-2-imidazolyl, 2-hexyl-5imidazolyl, 4-methyl-2-pyrimidyl, 2-propyl-3-pyrazinyl, 2-methyl-6-quinolyl, 2-methyl-5-benzimidazolyl, 5-ethyl-2benzimidazolyl, 3-methyl-5-indolyl, 5-methyl-2-isoindolyl, 2-methyl-4-isoindolyl, 4-methyl-6-cinnolyl, 2-methyl-8group quinoxalyl, 1-methyl-7-phthalazyl, 7-methyl-6-quinazolyl, 6-methyl-3-benzo[b]furyl, 7-methyl-5-benzo[b]thienyl, 2oxoquinolyl, 2-oxo-3-pyrrolidinyl, 3-oxo-2-piperazinyl, and the like.

The "phenyl having optionally a substituent selected from a halogen atom and a lower alkoxy on the phenyl ring" includes a phenyl group which may optionally have one to three substituents selected from a straight chain or branched chain alkoxy group having 1 to 6 carbon atoms and a halogen atom, for example, phenyl, 2-methoxyphenyl, 3-methoxyphenyl, 4-methoxyphenyl, 2-ethoxyphenyl, 3-ethoxyphenyl, 4-ethoxyphenyl, 4-isopropoxyphenyl, 4-pentyloxyphenyl, 2,4-dimethoxyphenyl, 4-hexyloxyphenyl, 3,4-dimethoxyphenyl, 3-ethoxy-4-methoxyphenyl, 2,3-dimethoxyphenyl, 3,4-diethoxyphenyl, 2,5-dimethoxyphenyl, 2,6-dimethoxyphenyl, 3,5-dimethoxyphenyl, 3,4-dipentyloxyphenyl, 3,4,5-trimethoxyphenyl, 2-chlorophenyl, 3-chlorophenyl, 4-chlorophenyl, 2-fluorophenyl, 3-fluorophenyl, 4-fluorophenyl, 2-bromophenyl, 3-bromophenyl, 4-bromophenyl, 2-iodophenyl, 3-iodophenyl, 4-iodophenyl, 3,4-dichlorophenyl, 3,5-dichlorophenyl, 2,6-dichlorophenyl, 2,3"dichlorophenyl, 2,4-dichlorophenyl, 3,4-difluorophenyl, 3,5-dibromophenyl, 3,4,5-trichlorophenyl, 2-methoxy-3-chlorophenyl, and the like.

The "phenylthio having optionally a substituent selected from nitro and amino" includes a phenylthio group having optionally one to three substituents selected from nitro group and amino group on the phenyl ring, for example, phenylthio, 2-nitrophenylthio, 3-nitrophenylthio, 4-nitrophenylthio, 2-aminophenylthio, 3-aminophenylthio, 4-aminophenylthio, 2,4-dinitrophenylthio, 2,4,6-trinitrophenylthio, 2,4-diaminophenylthio, 2,4,6-triaminophenylthio, 2-nitro-4-aminophenylthio, and the like.

The alkenylthio" includes a straight chain or branched chain alkenylthio group having 2 to 6 carbon atoms, for example, vinylthio, allylthio, 2-butenylthio, 3-butenylthio, 1-methylallylthio, 2-pentenylthio, 2-hexenylthio, and the like.

The "pyrrolidinyl-substituted lower alkylthio" includes a pyrrolidinyl-substituted alkylthio group wherein the alkylthio moiety is a straight chain or branched chain alkylthio group having 1 to 6 carbon atoms, for example, (1-pyrrolidinyl)methylthio, 2-(2-pyrrolidinyl)ethylthio, 1-(3-pyrrolidinyl)ethylthio, 3-(1-pyrrolidinyl)propylthio, 4-(1-pyrrolidinyl)butylthio, 5-(2-pyrrolidinyl)pentylthio, 6-(3-pyrrolidinyl)hexylthio, 1,1-dimethyl-2-(1-pyrrolidinyl)-ethylthio, 2-methyl-3-(1-pyrrolidinyl)propylthio, and the like.

The "pyrrolidinyl-substituted lower alkylsulfinyl" includes a pyrrolidinyl-substituted alkylsulfinyl group wherein the alkylsulfinyl moiety is a straight chain or branched chain alkylsulfinyl group having 1 to 6 carbon atoms, for example, (1-pyrrolidinyl)methylsulfinyl, 2-(2-pyrrolidinyl)ethylsulfinyl, 1-(3-pyrrolidinyl)ethylsulfinyl, 3-(1-pyrrolidinyl)propylsulfinyl, 4-(1-pyrrolidinyl)butylsulfinyl, 5-(2-pyrrolidinyl)pentylsulfinyl, 6-(3-pyrrolidinyl)hexylsulfinyl, 1,1-dimethyl-2-(1-pyrrolidinyl)ethylsulfinyl, 2-methyl-3-(1-pyrrolidinyl)propylsulfinyl, and the like.

The "pyrrolidinyl-substituted lower alkylsulfonyl" includes a pyrrolidinyl-substituted alkylsulfonyl group wherein the alkylsulfonyl moiety is a straight chain or branched chain alkylsulfonyl group having 1 to 6 carbon atoms, for example, (1-pyrrolidinyl)methylsulfonyl, 2-(2-pyrrolidinyl)ethylsulfonyl, 1-(3-pyrrolidinyl)ethylsulfonyl, 3-(1-pyrrolidinyl)propylsulfonyl, 4-(1-pyrrolidinyl)butylsulfonyl, 5-(2-pyrrolidinyl)pentylsulfonyl, 6-(3-pyrrolidinyl)hexylsulfonyl, 1,1-dimethyl-2-(1-pyrrolidinyl)-ethylsulfonyl, 2-methyl-3-(1-pyrrolidinyl)propylsulfonyl, and the like.

The "lower alkylthio" includes a straight chain or branched chain alkylthio group having 1 to 6 carbon atoms, for example, methylthio, ethylthio, propylthio, isopropylthio, butylthio, tert-butylthio, pentylthio, hexylthio, and the like.

The carbostyril derivatives of the present invention can be prepared by various processes, for example, by the processes shown in the following reaction schemes.

[Reaction Scheme-1]

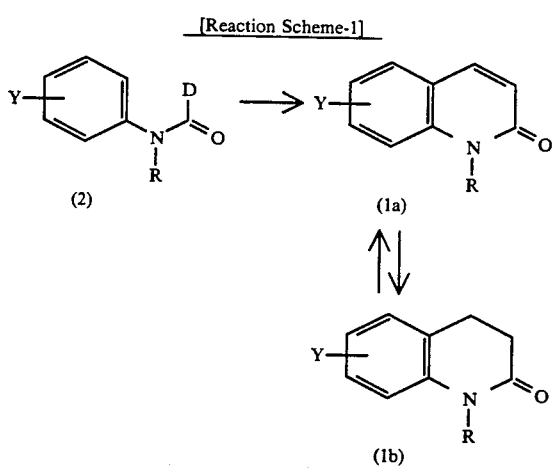

wherein R is the same $R^4$ as defined above or a group of the formula:

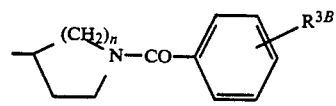

wherein n and $R^{3B}$ are the same as defined above, and D is a group of the formula: —CH=CHR$^{14'}$($R^{14'}$ is a lower alkoxy, phenyl or a halogen atom), a group of the formula:

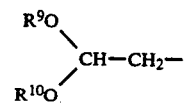

($R^9$ and $R^{10}$ are each a lower alkyl), or a group of the formula: —C≡CH, and Y is hydrogen atom or a lower alkyl. The cyclization reaction of the compound of the formula (2) is carried out in an appropriate solvent or without solvent in the presence of an acid. The acid includes any conventional inorganic acids and organic acids, for example, inorganic acids (e.g. hydrochloric acid, hydrobromic acid, sulfuric acid, phosphorus pentoxide, polyphosphoric acid, etc.), Lewis acids (e.g. aluminum chloride, boron trifluoride, titanium tetrachloride, etc.), organic acids (e.g. formic acid, acetic acid, ethanesulfonic acid, p-toluenesulfonic acid, etc.), among which hydrochloric acid, hydrobromic acid and sulfuric acid are preferable. The acid is usually used in at least equivalent amount, preferably in an amount of 10 to 50 times by weight, as much as the amount of the compound (2). The solvent includes any conventional inert solvents, for example, water, lower alcohols (e.g. methanol, ethanol, propanol, etc.), ethers (e.g. dioxane, tetrahydrofuran, etc.), aromatic hydrocarbons (e.g. benzene, chlorobenzene, toluene, etc.), halogenated hydrocarbons (e.g. methylene chloride, chloroform, carbon tetrachloride, etc.), acetone, dimethylsulfoxide, dimethylformamide, hexamethylphosphoric triamide, and the like. The reaction is usually carried out at a temperature of from about 0 to about 200° C., preferably from room temperature to about 150° C., for about 5 minutes to 6 hours.

The reduction of the compound of the formula (Ia) is usually carried out under conventional conditions for the usual catalytic reduction. The catalyst includes metals such as palladium, palladium-carbon, platinum, Raney nickel, etc. These metals are used in a conventional catalytic amount. The solvent used therein includes, for example, alcohols (e.g. methanol, ethanol, isopropanol, etc.), ethers (e.g. dioxane, tetrahydrofuran, etc.), aliphatic hydrocarbons (e.g. hexane, cyclohexane, etc.), esters (e.g. ethyl acetate, etc.), fatty acids (e.g. acetic acid, etc.). The reduction reaction can be carried out under atmospheric pressure or under pressure, usually under atmospheric pressure to 20 kg/cm², preferably atmospheric pressure to 10 kg/cm². The reaction temperature is usually in the range of from about 0° C. to about 150° C., preferably from room temperature to about 100° C.

The dehydrogenation reaction of the compound of the formula (Ib) is usually carried out in an appropriate solvent with an oxidizing agent. The oxidizing agent includes, for example, benzoquinones (e.g. 2,3-dichloro-5,6-dicyanobenzoquinone, chloranil (=2,3,5,6-tetrachlorobenzoquinone), etc.), halogenating agents (e.g. N-bromosuccinimide, N-chlorosuccinimide, bromine, etc.), hydrogenating catalysts (e.g. selenium oxide, palladium-carbon, palladium black, palladium oxide, Raney nickel, etc.). When a halogenating agent is used, it is used in a wide range of amount but is usually used in an amount of 1 to 5 moles, preferably 1 to 2 moles, to 1 mole of the compound (Ib). When a hydrogenating catalyst is used, it is used in a catalytic amount as usual. The solvent includes, for example, ethers (e.g. dioxane, tetrahydrofuran, methoxyethanol, dimethoxyethane, etc.), aromatic hydrocarbons (e.g. benzene, toluene, xylene, cumene, etc.), halogenated hydrocarbons (e.g. dichloromethane, dichloroethane, chloroform, carbon tetrachloride, etc.), alcohols (e.g. butanol, amyl alcohol, hexanol, etc.), polar protic solvents (e.g. acetic acid, etc.), aprotic polar solvents (e.g. dimethylformamide, dimethylsulfoxide, hexamethylphosphoric triamide, etc.). The reaction is usually carried out at a temperature of from room temperature to about 300° C., preferably from room temperature to about 200° C., for 1 to 40 hours.

[Reaction Scheme-2]

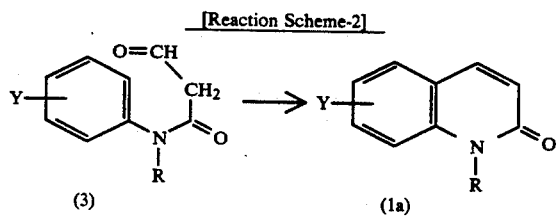

wherein R and Y are the same as defined above.

The cyclization reaction of the compound (3) is carried out in an appropriate solvent in the presence of a condensation agent. The condensation agent includes, for example, Lewis acids, such as phosphorus pentoxide, hydrogen fluoride, sulfuric acid, polyphosphoric acid, aluminum chloride, zinc chloride, etc. The solvent includes, for example, halogenated hydrocarbons (e.g. chloroform, dichloromethane, 1,2-dichloroethane, etc.),ethers (e.g. diethyl ether, dioxane, etc.), aromatic hydrocarbons (e.g. nitrobenzene, chlorobenzene, etc.). The condensation agent is usually used in an amount of about 1 to 10 moles, peferably about 3 to 6 moles, to 1 mole of the compound (3). The reaction is usually carried out at a temperature of about 50° C. to about 250° C., peferably about 70° C. to about 200° C., for about 20 minutes to about 6 hours.

[Reaction Scheme-3]

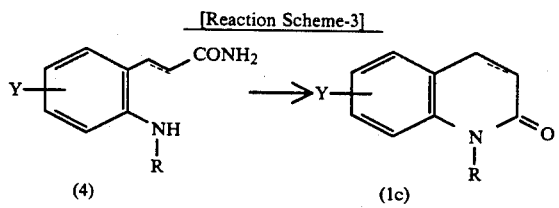

wherein R, Y and the bond between 3- and 4-positions of the carbonstyril nucleus are the same as defined above.

The cyclization reaction of the compound (4) is carried out in an appropriate solvent or without using a solvent in the presence of an acid. The acid includes, for example, inorganic acids (e.g. hydrochloric acid, sulfuric acid, hydrobromic acid, nitric acid, polyphosphoric acid, etc.), organic acids (e.g. p-toluenesulfonic acid, ethanesulfonic acid, trifluoroacetic acid, etc.). The solvent includes any conventional solvents unless they affect on the reaction, for example, water, alcohols (e.g. methanol, ethanol, propanol, butanol, 3-methoxy-1-butanol, ethyl-cellosolve, methylcellosolve, etc.), pyridine, acetone, halogenated hydrocarbons (e.g. methylene chloride, chloroform, dichloroethane, etc.), aromatic hydrocarbons (e.g. benzene, toluene, xylene, etc.), ethers (e.g. diethyl ether, tetrahydrofuran, dimethoxyethane, diphenyl ether, etc.), esters (e.g. methyl acetate, ethyl acetate, etc.), aprotic polar solvents (e.g. N,N-dimethylformamide, dimethylsulfoxide, hexamethylphosphoric triamide, etc.), or a mixture of these solvents. The reaction is usually carried out at a temperature of from about −20° C. to about 150° C., preferably from about 0° C. to about 150° C., for about 5 minutes to about 30 hours.

[Reaction Scheme-4]

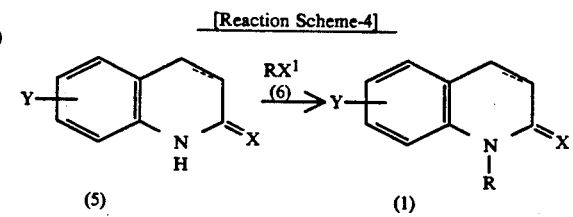

wherein R, X, Y and the bond between 3- and 4-positions of the carbostyril nucleus are the same as defined above, and $X^1$ is a halogen atom.

The reaction of the compound of the formula (5) and the compound of the formula (6) is usually carried out in an appropriate inert solvent in the presence or absence of a basic compound. The inert solvent includes, for example, aromatic hydrocarbons (e.g. benzene, toluene, xylene, etc.), alcohols (e.g. methanol, ethanol, propanol, butanol, 3-methoxy-1-butanol, ethylcellosolve, methylcellosolve, etc.), pyridine, acetone, N-methylpyrrolidone, dimethylsulfoxide, dimethylformamide, hexamethylphosphoric triamide, etc. The basic compound includes, for example, sodium carbonate, potassium carbonate, sodium hydrogen carbonate, potassium hydrogen carbonate, sodium hydroxide, potassium hydroxide, sodium hydride, potassium hydride, triethylamine, etc.

The amounts of the compound (5) and the compound (6) are not critical, but the compound (6) is usually used at least in equimolar amount, preferably in an amount of 1 to 5 moles to 1 mole of the compound (5). The reaction is usually carried out at a temperature of from room temperature to about 200° C., preferably about 100° C. to about ° C., for about 3 to 30 hours. In the above reaction, a copper powder may also be used as a catalyst, by which the reaction can proceed advantageously.

[Reaction Scheme-5A]

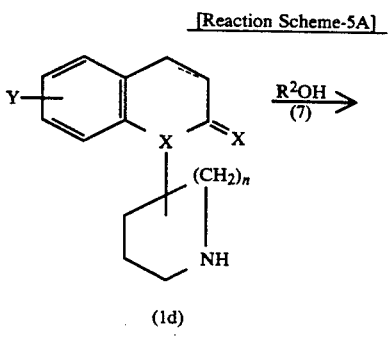

-continued
[Reaction Scheme-5A]

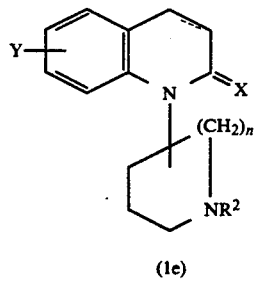

(1e)

wherein X, Y, n and the bond between 3- and 4-positions of the carbostyril nucleus are the same as defined above, and $R^2$ is the same as $R^{2A}$ as mentioned above or a group of the formula:

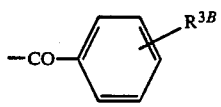

($R^{3B}$ is the same as defined above).

[Reaction Scheme-5B]

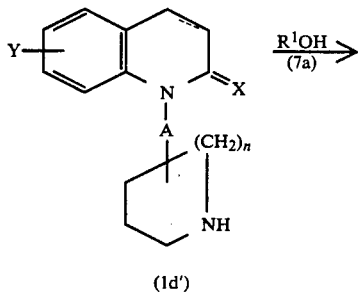

(1d')

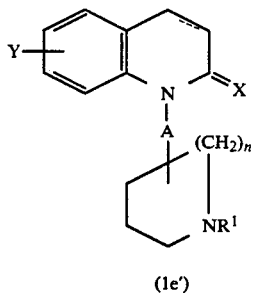

(1e')

wherein $R^1$, X, Y, A, n and the bond between 3- and 4-positions of the carbostyril nucleus are the same as defined above.

The process of Reaction Schemes-5A and -5B is carried out by reacting a carbostyril derivative of the formula (1d) or (1d') and a carboxylic acid compound of the formula (7) or (7a) by a conventional amido bond producing reaction. The amido bond producing reaction can be carried out under the conditions for the conventional amido bond producing reaction, for example, (a) a mixed acid anhydride process, i.e. a process of reacting the carboxylic acid compound (7) or (7a) with an alkyl-halocarboxylic acid to form a mixed acid anhydride and reacting the resultant with the amine compound (1d) or (1d'), (b) an activated ester process, i.e. a process of converting the carboxylic acid compound (7) or (7a) into an activated ester, such as p-nitrophenyl ester, N-hydroxysuccinimide ester, 1-hydroxybenzotriazole ester, etc., and reacting the resultant with the amine compound (1d) or (1d'), (c) a carbodiimide process, i.e. a process of condensing the carboxylic acid compound (7) or (7a) and the amine compound (1d) or (1d') in the presence of an activating agent such as dicyclohexylcarbodiimide, carbonyldiimidazole, etc., (d) other processes, i.e. a process of converting the carboxylic acid compound (7) or (7a) into a carboxylic anhydride by treating it with a dehydrating agent such as acetic anhydride, and reacting the resultant with the amine compound (1d) or (1d'); a process of reacting an ester of the carboxylic acid compound (7) or (7a) with a lower alcohol and the amine compound (1d) or (1d') at a high temperature under high pressure; a process of reacting an acid halide compound of the carboxylic acid compound (7) or (7a), i.e. a carboxylic acid halide, with the amine compound (1d) or (1d'), and the like.

The mixed acid anhydride used in the above mixed acid anhydride process is obtained by the known Schötten-Baumann tten-Baumann reaction, and the reaction product is used without isolation from the reaction mixture for the reaction with the amine compound (1d) or (1d') to give the desired compound of the formula (1e) or (1e'). The Schötten-Baumann reaction is usually carried out in the presence of a basic compound. The basic compound is any conventional compounds used for the Schötten-Baumann reaction and includes, for example, organic basic compounds such as triethylamine, trimethylamine, pyridine, dimethylaniline, N-methylmorpholine, 1,5-diazabicyclo[4.3.0]nonene-5 (DBN), 1,8-diazabicyclo[5.4.0]undecene-7 (DBU), 1,4-diazabicyclo[2.2.2]octane (DABCO), etc., and inorganic basic compounds such as potassium carbonate, sodium carbonate, potassium hydrogen carbonate, sodium hydrogen carbonate, etc. The reaction is usually carried out at a temperature of from about $-20°$ C. to about $100°$ C., preferably from about $0°$ C. to about $50°$ C., for about 5 minutes to about 10 hours, preferably about 5 minutes to about 2 hours.

The reaction of the thus obtained mixed acid anhydride with the amine compound (1d) or (1d') is usually carried out at a temperature of from about $-20°$ C. to about $150°$ C., preferably about $10°$ C. to about $50°$ C., for about 5 minutes to about 10 hours, preferably about 5 minutes to about 5 hours. The mixed acid anhydride process is usually carried out in an appropriate solvent. The solvent is any conventional solvents which are usually used in the mixed acid anhydride process and includes, for example, halogenated hydrocarbons (e.g. methylene chloride, chloroform, dichloroethane, etc.), aromatic hydrocarbons (e.g. benzene, toluene, xylene, etc.), ethers (e.g. diethyl ether, diisopropyl ether, tetrahydrofuran, dimethoxyethane, etc.), esters (e.g. methyl acetate, ethyl acetate, etc.), aprotic polar solvents (e.g. N,N-dimethylformamide, dimethylsulfoxide, hexamethylphosphoric triamide, etc.), or a mixture of these solvents. The alkylhalocarboxylic acid used in the mixed acid anhydride process includes, for example, methyl chloroformate, methyl bromoformate, ethyl chloroformate, ethyl bromoformate, isobutyl chloroformate, and the like. In said process, the carboxylic acid compound (7) or (7a), the alkylhalocarboxylic acid and the amine (1d) or (1d') are usually used in each equimolar amount, but preferably, the alkylhalocarboxylic acid and the carboxylic acid compound (7) or (7a) are used each in an amount of about 1 to 1.5 mole to 1 mole of the amine (1d) or (1d').

Among the above other processes (d), in case of the process of reacting the carboxylic acid halide with the amine compound (1d) or (1d'), the reaction is usually carried out in the presence of a basic compound in an appropriate solvent. The basic compound is any conventional compounds and includes, in addition to the basic compounds used for the above-mentioned Schötten-Baumann reaction, sodium hydroxide, potassium hydroxide, sodium hydride, potassium hydride. etc. The solvent includes, in addition to the solvents used for the above-mentioned mixed acid anhydride process, alcohols (e.g. methanol, ethanol, propanol, butanol, 3-methoxy-1-butanol, ethylcellosolve, methylcellosolve, etc.), acetonitrile, pyridine, acetone, and the like. The amount of the amine compound (1d) or (1d') and the carboxylic acid halide is not critical, but the carboxylic acid halide is usually used at least in equimolar amount, preferably about 1 to 5 moles to 1 mole of the amine compound (1d) or (1d'). The reaction is usually carried out at a temperature of from about −20° C. to about 180° C., preferably from about 0° C. to about 150° C., for about 5 minutes to about 30 hours.

The amido bond producing reaction in the above Reaction Schemes-5A and -5B may also be carried out by reacting the carboxylic acid compound (7) or (7a) and the amine (1d) or (1d') in the presence of a condensation agent such as triphenylphosphine, diphenylphosphinyl chloride, phenyl-N-phenylphosphoramide chloridate, diethyl chlorophosphate, diethyl cyanophosphate, bis(2-oxo-3-oxazolidinyl)phosphinic chloride, etc. The reaction is usually carried out in the presence of the solvent and basic compound as used in the above reaction of the carboxylic acid halide and the amine (1d) or (1d') at a temperature of from about −20° C. to about 150° C., preferably about 0° C to about 100° C., for about 5 minutes to about 30 hours. The condensation agent and the carboxylic acid compound (7) or (7a) are used at least in equimolar amount, preferably about to 2 moles, to 1 mole of the amine (1d) or (1d').

[Reaction Scheme-6A]

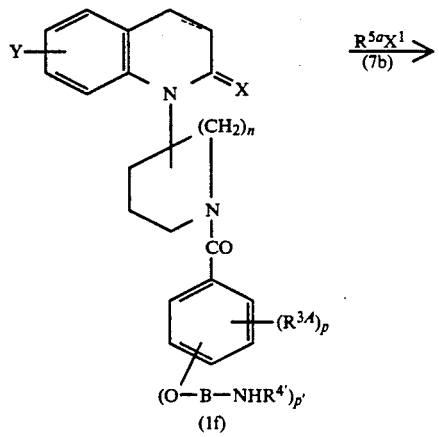

(1f)

[Reaction Scheme-6A]
-continued

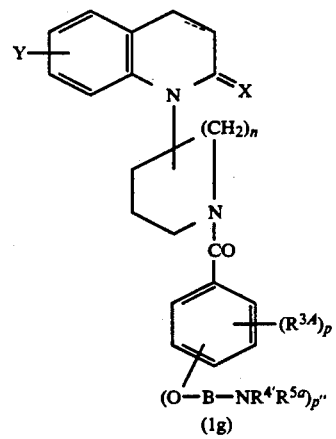

(1g)

wherein X, Y, n, $R^3A$, $X^1$, B, A, and the bond between 3- and 4-positions of the carbostyril nucleus are the same as defined above, and $R^{4'}$ is hydrogen atom, $R^{5a}$ is tricyclo-[3.3.1.]decany, a tricyclo[3.3.1.1]decanyl-lower alkyl, a halogen-substituted lower alkyl, a lower alkoxycarbonyl-lower alkanoyloxy-lower alkyl, or a lower alkenyl, and p' and p" are each an integer of 1 to 3, provided that p+p' and p+p" are each an integer not more than 3.

[Reaction Scheme-6B]

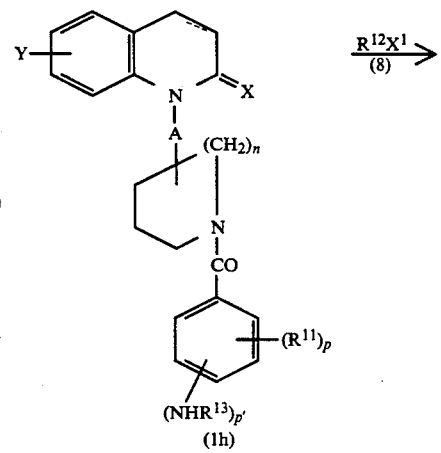

(1h)

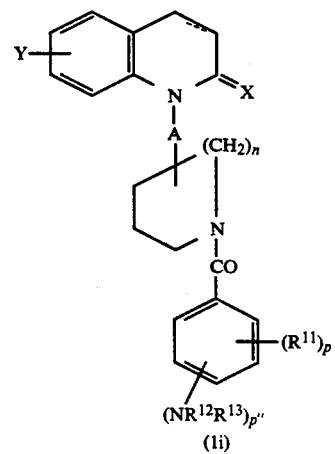

(1i)

wherein X, Y, n, $X^1$, A, and the bond between 3- and 4-positions of carbostyril nucleus are the same as defined above, and $R^{11}$ is an amino being optionally substituted by a lower alkoxy or a lower alkyl, $R^{12}$ is a lower alkyl, $R^{13}$ is hydrogen atom or a lower alkyl, and p′ and p″ are each an integer of 1 to 3, provided that p+p′ and p+p″ are each an integer not more than 3.

[Reaction Scheme-6C]

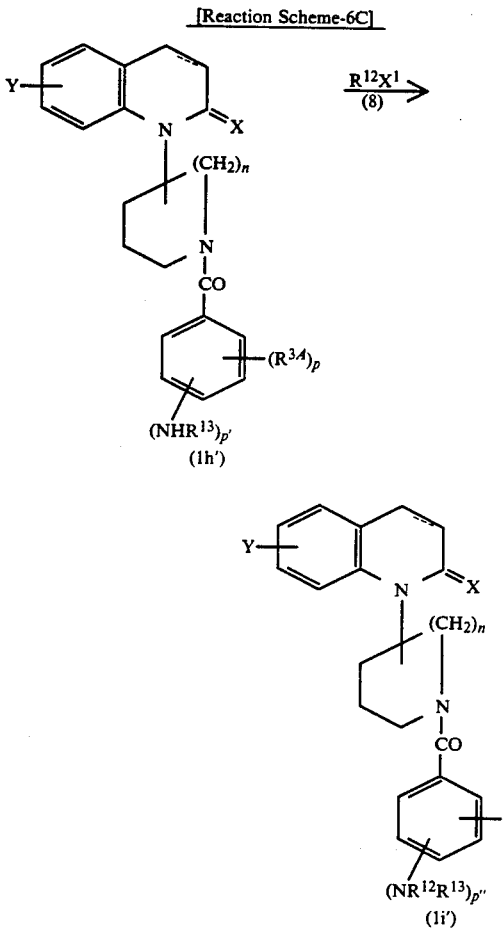

wherein X, Y, n, $R^{3A}$, $X^1$, $R^{12}$, $R^{13}$, and the bond between 3- and 4-positions of carbostyril nucleus are the same as defined above, and p′ and p″ are each an integer of 1 to 3, provided that p+p′0 and p+p″ are each an integer not more than 3.

The reaction of the compound (1f) and the compound (7b) in Reaction Scheme-6A, the reaction of the compound (1h) and the compound (8) in Reaction Scheme-6B, and the reaction of the compound (1h′) and the compound (8) in Reaction Scheme-6C are usually carried out in an inert solvent in the presence or absence of a basic compound. The inert solvent includes, for example, aromatic hydrocarbons (e.g. benzene, toluene, xylene, etc.), ethers (e.g. tetrahydrofuran, dioxane, diethylene glycol dimethyl ether, etc.), lower alcohols (e.g. methanol, ethanol, isopropanol, butanol, etc.), halogenated hydrocarbons (e.g. dichloromethane, dichlcroethane, chloroform, carbon tetrachloride, etc.), acetic acid, ethyl acetate, acetone, acetonitrile, dimethylsulfoxide, dimethylformamide, hexamethylphosphoric triamide, and the like. The basic compound includes, for example, metal carbonates (e.g. sodium carbonate, potassium carbonate, sodium hydrogen carbonate, potassium hydrogen carbonate, etc.), metal hydroxides (e.g. sodium hydroxide, potassium hydroxide, etc.), sodium hydride, potassium, sodium, sodium amide, metal alcoholates (e.g. sodium methoxide, sodium ethoxide, etc.), and organic basic compounds (e.g. pyridine, ethyldiisopropylamine, dimethylaminopyridine, triethylamine, 1,5-diazabicyclo[4.3.0]nonene(5) (DBN), 1,8-diazabicyclo[5.4.0]undecene-7 (DBU), 1,4-diazabicyclo[2.2.2]octane (DABCO), etc.). The ratio of the compound (7b) or (8) to the compound (1f), (1h) or (1h′) is not critical, but the compound (7b) or (8) is usually used at least in equivalent amount, preferably 1 to 5 moles, to 1 mole of the compound (1f), (1h) or (1h′). The reaction is usually carried out at a temperature of from about 0° C. to about 200° C., preferably from about 0° C. to about 170° C, for about 30 minutes to about 30 hours.

Moreover, the compounds (1i) and (1i′) wherein $R^{12}$ is a lower alkyl can also be obtained by reacting the compound (1h) or (1h′) with a compound of the formula:

$$R^{14}-CO-R^{15} \qquad (9)$$

wherein $R^{14}$ and $R^{15}$ are each hydrogen atom or a lower alkyl, respectively.

The reaction is usually carried out in an appropriate solvent or without solvent in the presence of a reducing agent. The solvent includes, for example, water, alcohols (e.g. methanol, ethanol, isopropanol, etc.), acetonitrile, formic acid, acetic acid, ethers (e.g. dioxane, diethyl ether, diglyme, tetrahydrofuran, etc.), aromatic hydrocarbons (e.g. benzene, toluene, xylene, etc.), or a mixture of these solvents. The reducing agent includes, for example, formic acid, fatty acid alkali metal salts (e.g. sodium formate., etc.), hydrogenating reducing agents (e.g. sodium borohydride, sodium cyanoborohydride, lithium aluminum hydride, etc.), catalytic reducing agents (e.g. palladium black, palladium-carbon, platinum oxide, platinum black, Raney nickel, etc.). When formic acid is used as the reducing agent, the reaction is usually carried out at a temperature of from room temperature to about 200° C., peferably about 50° C. to about 150° C., for about 1 to 10 hours. The formic acid is usually used in a large excess amount to the compound (1h) or (1h′).

When a hydrogenating reducing agent is used, the reaction is usually carried out at a temperature of about −30° C. to about 100° C., preferably about 0° C. to about 70° C., for about 30 minutes to about 12 hours. The reducing agent is usually used in an amount of 1 to 20 moles, preferably 1 to 6 moles, to 1 mole of the compound (1h) or (1h′). When lithium aluminum hydride is used as the reducing agent, it is preferable to use a solvent selected from ethers (e.g. diethyl ether, dioxane, tetrahydrofuran, diglyme, etc.) and aromatic hydrocarbons (e.g. benzene, toluene, xylene, etc.).

When a catalytic reducing agent is used, the reaction is usually carried out under atmospheric pressure to about 20 atm., preferably atmospheric pressure to about 10 atm. under hydrogen atmosphere or in the presence of a hydrogen donor (e.g. formic acid, ammonium formate, cyclohexene, hydrazine hydrate, etc.) at a temperature of about −30° C. to about 100° C., preferably about 0° C. to about 60° C., for about 1 to 12 hours. The catalytic reducing agent is usually used in an amount of about 0.1 to 40 % by weight, preferably about 1 to 20 % by weight, of the amount of the compound (1h) or (1h′). The compound (9) is usually used at least in equivalent amount, preferably equivalent to a large excess amount, to the compound (1h) or (1h').

[Reaction Scheme-7]

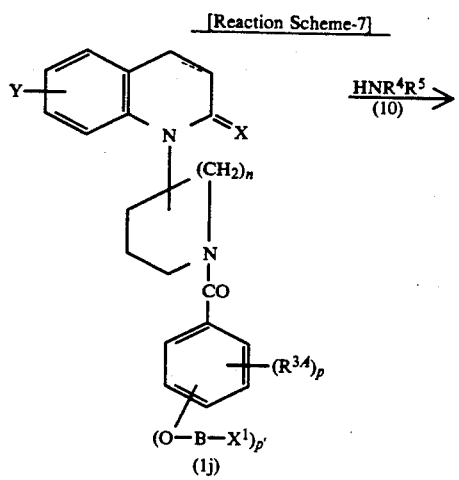

(1j)

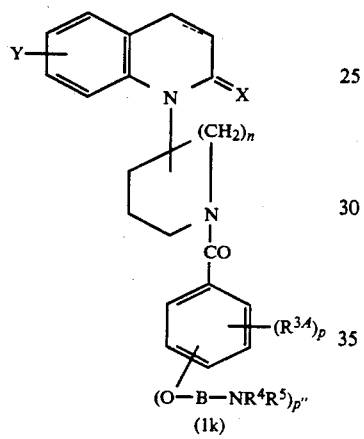

(1k)

wherein X, Y, p, $R^{3A}$, n, $R^4$, , $R^5$, p', p", B, $X^1$, and the bond between 3- and 4-positions of the carbostyril nucleus are the same as defined above.

The reaction of the compound (1j) and the compound (10) is carried out under the same conditions as in the reaction of the compound (1f) and the compound (7b) in the above Reaction Scheme-6A.

[Reaction Scheme-8]

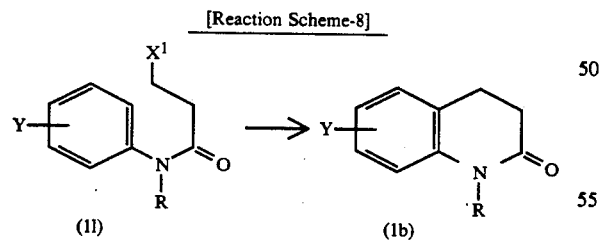

wherein R, Y and $X^1$ are the same as defined above.

The cyclization reaction of the compound (11) is so-called Friedel Craft reaction and is usually carried out in an appropriate solvent in the presence of a Lewis acid. The solvent includes any conventional solvent which is usually used in this kind of reaction, for example, carbon disulfide, nitrobenzene, chlorobenzene, dichloromethane, dichloroethane, trichloroethane, tetrachloroethane, and the like. The Lewis acid includes any conventional acid, for example, aluminum chloride, zinc chloride, iron chloride, tin chloride, boron tribromide, boron trifluoride, conc. sulfuric acid, and the like. The amount of Lewis acid is not critical but is usually in the range of about 2 to 6 moles, preferably about 3 to 4 moles, to 1 mole of the compound (1l). The reaction temperature is usually in the range of about 20° C. to 200° C., preferably 40° C. to 180° C. The reaction period of time may vary depending on the kinds of the starting compound, catalyst and reaction temperature, etc., but is usually in the range of about 0.5 to 6 hours. Besides, sodium chloride may be added to the reaction system in order to proceed the reaction advantageously.

[Reaction Scheme-9]

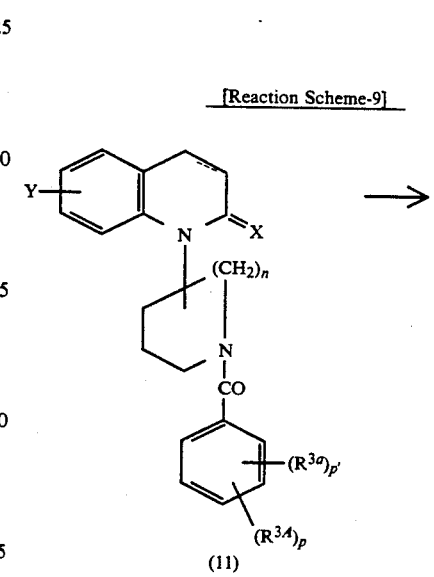

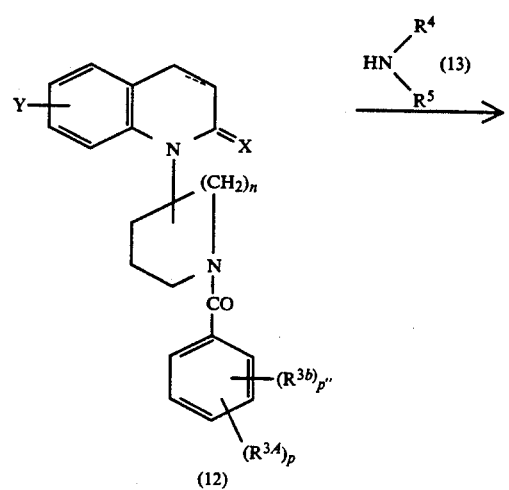

-continued

[Reaction Scheme-9]

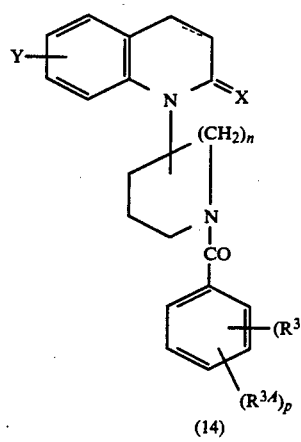

(14)

wherein X, Y, R³A, n, p, p', p", and the bond between 3- and 4-positions of the carbostyril nucleus are the same as defined above, and $R^{3a}$ is a lower alkenyloxy, $R^{3b}$ is an oxilanylsubstituted lower alkoxy, $R^{3c}$ is a lower alkoxy having a substituent selected from a group of the formula:

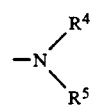

($R^4$ and $R^5$ are as defined above) and hydroxy, and p''' is an integer of 1 to 3, provided that p+p''' is not more than 3.

The reaction of converting the compound (11) into the compound (12) is carried out in an appropriate solvent in the presence of an oxidizing agent. The solvent includes, for example, water, organic acids (e.g. formic acid, acetic acid, trifluoroacetic acid, etc.), alcohols (e.g. methanol, ethanol, etc.), halogenated hydrocarbons (e.g. chloroform, dichloromethane, etc.), or a mixture of these solvents. The oxidizing agent includes, for example, peracids (e.g. performic acid, peracetic acid, trifluoroperacetic acid, perbenzoic acid, m-chloro-perbenzoic acid, o-carboxy-perbenzoic acid, etc.), hydrogen peroxide, sodium metaperiodate, dichromic acid, dichromates (e.g. sodium dichromate, potassium dichromate, etc.), permanganic acid, permanganates (e.g. potassium permanganate,.sodium permanganate, etc.), lead salts (e.g. lead tetraacetate, etc.), and the like. The oxidizing agent is usually used in an amount of at least 1 mole, preferably 1 to 2 moles, to 1 mole of the starting compound. The above reaction is usually carried out at a temperature of about 0° C. to about 40° C., preferably from about 0° C. to room temperature, for about 1 to 15 hours.

The reaction of the compound (12) and the compound (13) is carried out under the same conditions as in the reaction of the compound (1f) and the compound (7b) in the above Reaction Scheme-6A.

The starting compound (2) can be prepared, for example, by the processes as shown in the following Reaction Schemes-10 and -11.

[Reaction Scheme-10]

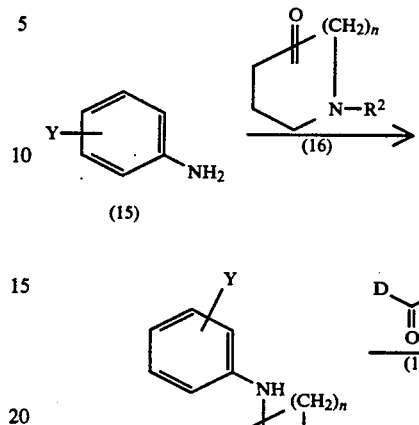

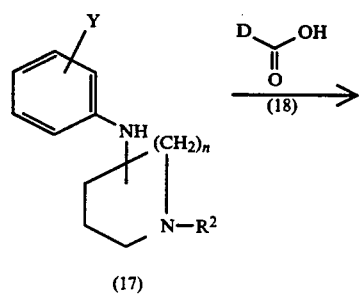

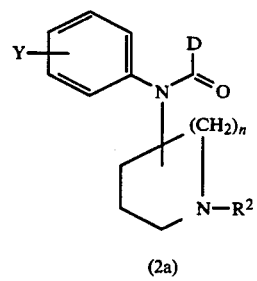

(2a)

wherein $R^2$, Y, n and D are the same as defined above.

The reaction of the compound (15) and the compound (16) is carried out under the same conditions as in the reaction of the compound (1H) and the compound (9) in the above Reaction Scheme-6B.

The reaction of the compound (17) and the compound (18) is carried out under the same conditions as in the reaction of the compound (1d) and the compound (7) in the above Reaction Scheme-5.

[Reaction Scheme-11]

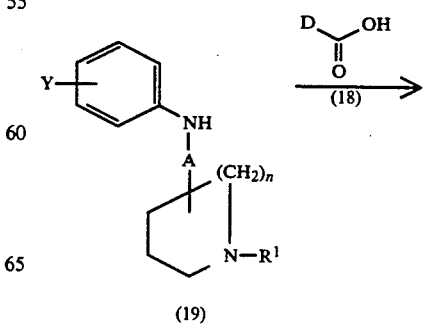

(19)

[Reaction Scheme-11]

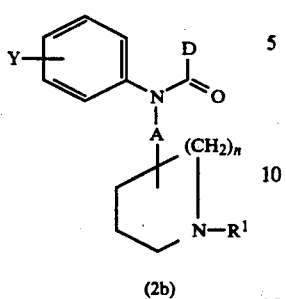

(2b)

wherein $R^1$, A, Y, n, and D are the same as defined above.

The reaction of the compound (19) and the compound (18) is carried out under the same conditions as the above reaction of the compound (17) and the compound (18).

The starting compound (4) can be prepared, for example, by the process of the following Reaction Scheme-12.

[Reaction Scheme-12]

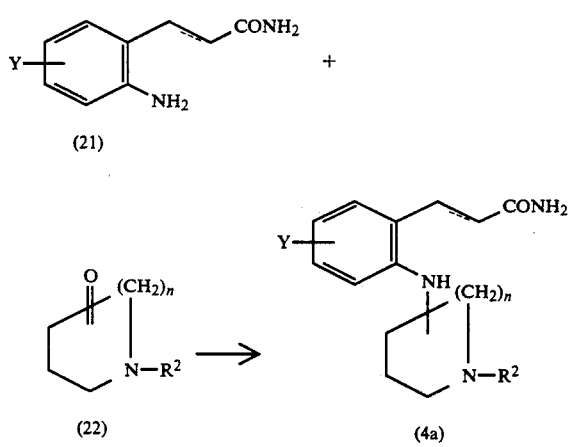

wherein $R^2$, Y, and n are the same as defined above.

The reaction of the compound (21) and the compound (22) is carried out under the same conditions as in the reaction of the compound (15) and the compound (16) in the above Reaction Scheme-10.

The starting compound (11) can be prepared, for example, by the process of the following Reaction Scheme-13.

[Reaction Scheme-13]

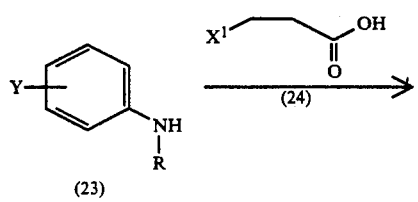

[Reaction Scheme-13] -continued

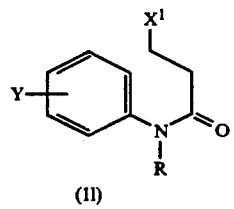

(11)

wherein R, Y and $X^1$ are as defined above.

The reaction of the compound (23) and the compound (24) is carried out under the same conditions as in the reaction of the compound (17) and the compound (18) in the above Reaction Scheme-10.

[Reaction Scheme-14]

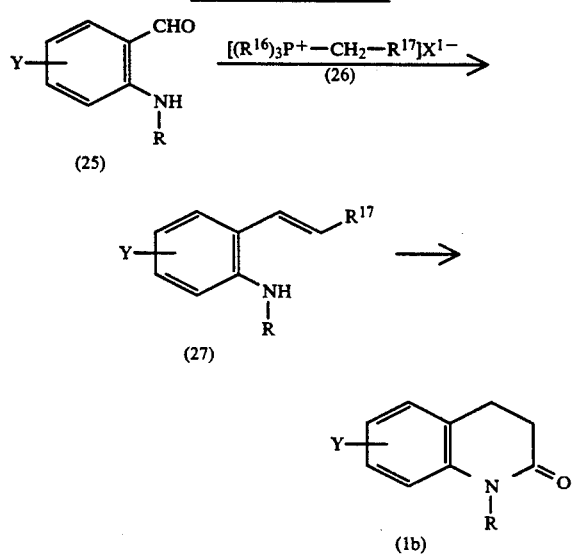

wherein R, Y and $X^1$ are the same as defined above, and $R^{16}$ is phenyl and $R^{17}$ is a lower alkoxycarbonyl.

The reaction of the compound (25) and the compound (26) is carried out in an appropriate solvent in the presence of a basic compound. The basic compound includes inorganic bases (e.g. sodium metal, potassium metal, sodium hydride, sodium amide, sodium hydroxide, potassium hydroxide, sodium carbonate, potassium carbonate, sodium hydrogen carbonate, etc.), metal alcoholates (e.g. sodium methylate, sodium ethylate, potassium t-butoxide, etc.), alkyl or aryl lithiums or lithium amides (e.g. methyl lithium, n-butyl lithium, phenyl lithium, lithium diisopropylamide, etc.), organic bases (e.g. pyridine, piperidine, quinoline, triethylamine, N,N-dimethylaniline, etc.). The solvent includes any solvent which does not affect on the reaction, for example, ethers (e.g. diethyl ether, dioxane, tetrahydrofuran, monoglyme, diglyme, etc.), aromatic hydrocarbons (e.g. benzene, toluene, xylene, etc.), aliphatic hydrocarbons (e.g. n-hexane, heptane, cyclohexane, etc.), amines (e.g. pyridine, N,N-dimethylaniline, etc.), aprotic polar solvents (e.g. N,N-dimethylformamide, dimethylsulfoxide, hexamethylphosphoric triamide, etc.), alcohols (e.g. methanol, ethanol, isopropanol, etc.), and the like. The reaction is usually carried out at a temperature of about −80° C. to about 150° C., preferably about −80° C. to about 120° C., for about 0.5 to 15 hours.

The cyclization reaction of the compound (27) is carried out in the presence of a catalytic reducing agent and in the presence or absence of a basic compound or an acid, preferably in the presence of an acid, in an appropriate solvent. The basic compound includes, for example, organic bases (e.g. triethylamine, trimethylamine, pyridine, dimethylaniline, N-methylmorpholine, DBN, DBU, DABCO, etc.), and inorganic bases (e.g. potassium carbonate, sodium carbonate, sodium hydroxide, potassium hydroxide, sodium hydride, potassium hydride, potassium hydrogen carbonate, sodium hydrogen carbonate, etc.), and the acid includes, for example, inorganic acids (e.g. hydrochloric acid, sulfuric acid, phosphoric acid, etc.), organic acids (e.g. acetic acid, etc.), or a mixture of these acids. The solvent includes, for example, water, alcohols (e.g. methanol, ethanol, propanol, butanol, 3-methoxy-1-butanol, ethylcellosolve, methylcellosolve, etc.), pyridine, acetone, halogenated hydrocarbons (e.g. methylene chloride, chloroform, dichloroethane, etc.), aromatic hydrocarbons (e.g. benzene, toluene, xylene, etc.), ethers (e.g. tetrahydrofuran, diethyl ether, dimethoxyethane, etc.), esters (e.g. methyl acetate, ethyl acetate, etc.), N,N-dimethylformamide, dimethylsulfoxide, hexamethylphosphoric triamide, or a mixture of these solvents. The catalytic reducing agent includes the same catalysts as used in the reduction reaction of the compound (1a) in the above Reaction Scheme-1. The reaction is usually carried out under atmospheric pressure to about 20 kg/cm$^2$, preferably atmospheric pressure to about 10 kg/cm$^2$, at a temperature of about 0° C. to about 200° C., preferably from room temperature to about 150° C., for about 1 to 10 hours. The catalytic reducing agent is preferably used in an amount of 0.02 to 1 part by weight to 1 part by weight of the compound (27).

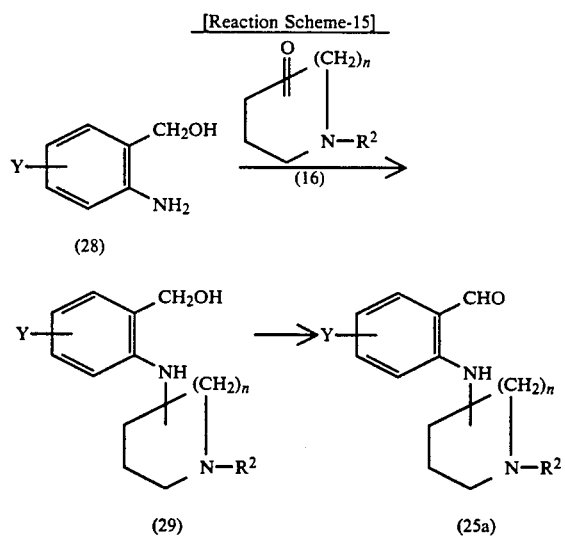

[Reaction Scheme-15]

wherein R$^2$, Y and n are as defined above.

The reaction of the compound (28) and the compound (16) is carried out under the same conditions as in the reaction of the compound (15) and the compound (16) in the above Reaction Scheme-10.

The reaction of converting the compound (29) into the compound (25a) is carried out in an appropriate solvent or without solvent in the presence of an oxidizing agent. The solvent includes the above-mentioned aromatic hydrocarbons, carbons, lower alcohols, halogenated hydrocarbons, ethers, polar solvents (e.g. dimethylsulfoxide, dimethylformamide, hexamethylphosphoric triamide, etc.). The oxidizing agent includes acetic anhydride-dimethylsulfoxide, phosphorus pentoxide-dimethylsulfoxide, sulfur trioxide.pyridine complex-dimethylsulfoxide, dicyclohexylcarbodiimidedimethylsulfoxide, oxalyl chloride-dimethylsulfoxide, chromic acid, chromic acid complexes (e.g. chromic acid-pyridine complex, chromic acid-2-pyridine complex, etc.), manganese dioxide, and the like. When oxalyl chloride-dimethylsulfoxide is used as the oxidizing agent, there may be added to the reaction system the basic compound as used in the reaction of the compound (1d) and the carboxylic halide in the above Reaction Scheme-5. The reaction is usually carried out at a temperature of 0° C. to 150° C., preferably from room temperature to about 100° C., for about 1 to 30 hours. The oxidizing agent is usually used in an amount of 1 to 20 moles, preferably 1 to 15 moles, to 1 mole of the compound (29).

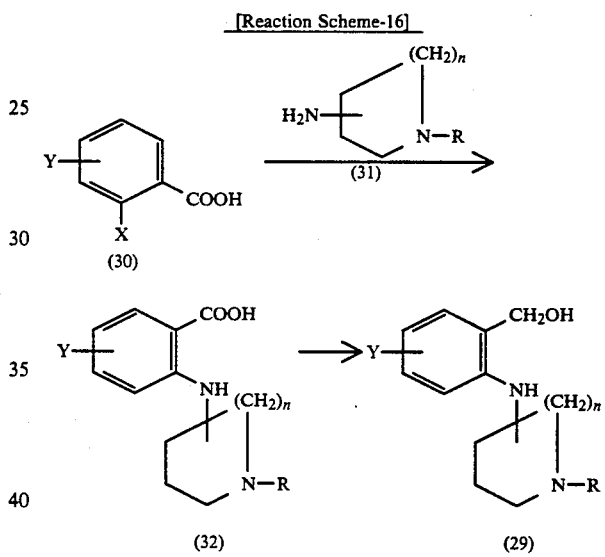

[Reaction Scheme-16]

wherein R, X, Y and n are the same as defined above.

The reaction of the compound (30) and the compound (31) is carried out under the same conditions as in the reaction of the compound (5) and the compound (6) in the above Reaction Scheme-4. In this reaction, copper monoxide may be added to the reaction system in order to proceed the reaction advantageously.

The reaction of converting the compound (32) into the compound (29) can be carried out by reducing the compound (32). The reduction reaction is preferably carried out by using a hydrogenating reducing agent. The hydrogenating reducing agent includes, for example, lithium aluminum hydride, sodium borohydride, diborane, and the like. The reducing agent is usually used at least in equimolar amount, preferably 1 to 15 moles, to 1 mole of the starting compound. The reducing reaction is usually carried out in an appropriate solvent, for example, water, lower alcohols (e.g. methanol, ethanol, isopropanol, etc.), ethers (e.g. tetrahydrofuran, diethyl ether, diisopropyl ether, diglyme, etc.), or a mixture of these solvents, at a temperature of about −60° C. to about 150° C., preferably −30° C. to 100° C., for about 10 minutes to about 5 hours. When lithium aluminum hydride or diborane is used as the reducing agent, it is preferable to use anhydrous solvents such as tetrahydrofuran, diethyl ether, diisopropyl ether, diglyme, etc.

[Reaction Scheme-17]

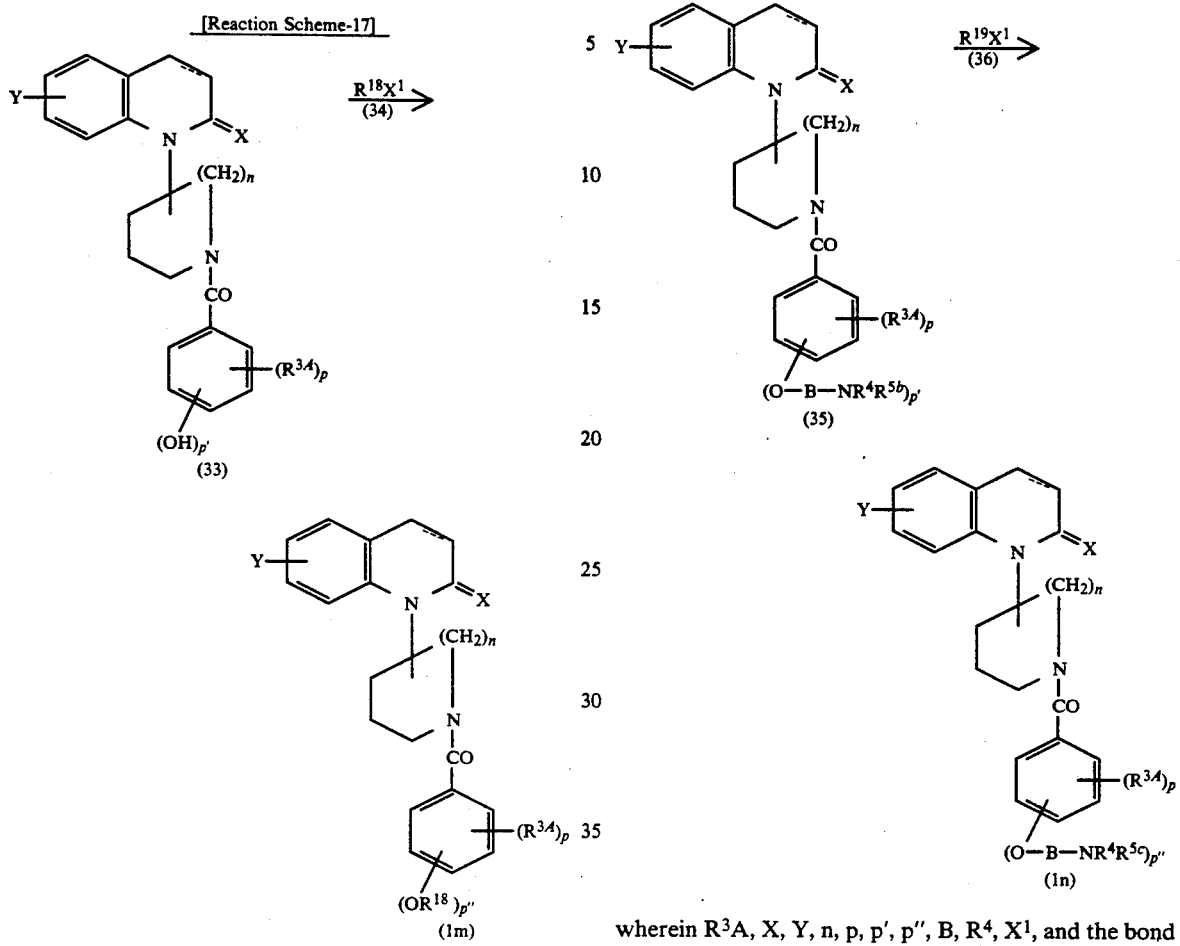

[Reaction Scheme-18]

wherein $R^{3A}$, X, Y, n, p, p', p", $X^1$, and the bond between 3-and 4-positions of the carbostyril nucleus are the same as defined above, and $R^{18}$ is a lower alkyl, a group of the formula:

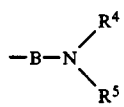

(B, $R^4$ and $R^5$ are the same as defined above), or a lower alkyl having two substituents selected from an aminocarbonyloxy having optionally a lower alkyl and a group of the formula:

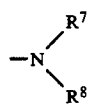

($R^7$ and $R^8$ are the same as defined above).

The reaction of the compound (33) and the compound (34) is carried out under the same conditions as in the reaction of the compound (1f) and the compound (7b) in the above Reaction Scheme-6A. In said reaction, an alkali metal halide (e.g. sodium iodide, potassium iodide, etc.) may be added to the reaction system.

wherein $R^{3A}$, X, Y, n, p, p', p", B, $R^4$, $X^1$, and the bond between 3- and 4-positions of the carbostyril nucleus are the same as defined above, and $R^{5b}$ is a hydroxy-substituted lower alkyl, $R^{5c}$ is a lower alkoxycarbonyl-lower alkanoyloxy-lower alkyl, and R19 is a lower alkoxycarbonyl-lower alkanoyl.

The reaction of the compound (35) and the compound (36) is carried out under the same conditions as in the reaction of the compound (1f) and the compound (7b) in the above Reaction Scheme-6A.

[Reaction Scheme-19]

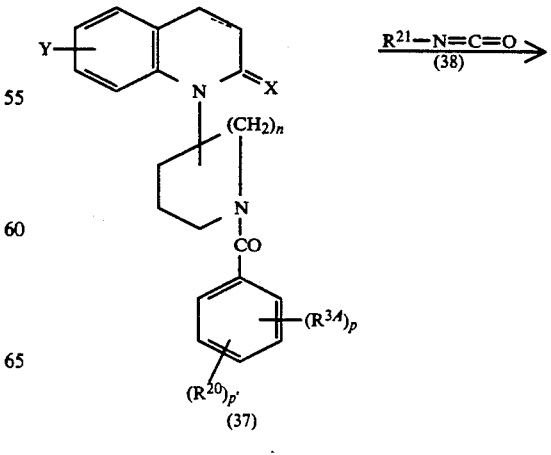

-continued
[Reaction Scheme-19]

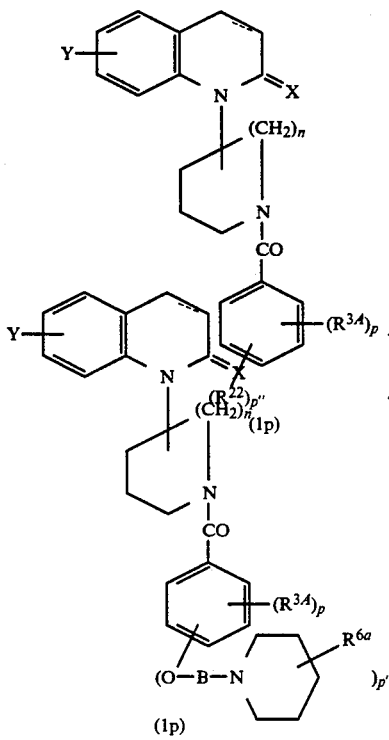

wherein X, Y, R³⁴, p, p′, p″, n, and the bond between 3- and 4-positions of the carbostyril nucleus are the same as defined above, and R²⁰ is a lower alkoxy having two substituents selected from hydroxy and a group of the formula:

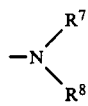

(R⁷ and R⁸ are the same as defined above), R²¹ is a lower alkyl, and R²² is an aminocarbonyloxy having optionally a lower alkyl substituent, or a group of the formula:

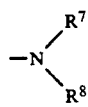

(R⁷ and R⁸ are the same as defined above).

The reaction of the compound (37) and the compound (38) is carried out in the presence or absence, preferably absence, of a basic compound in an appropriate solvent or without using any solvent. The solvent and basic compound used in the above reaction are the same solvents and basic compounds as used in the reaction of the amine (1d) and the carboxylic acid halide in the above Reaction Scheme-5. The compound (38) is usually used in an amount of about 1 to 5 moles, preferably about 1 to 3 moles, to 1 mole of the compound (37). The reaction is usually carried out at a temperature of about 0 to 200° C., preferably room temperature to about 150° C., for about 5 minutes to about 30 hours. In the reaction, a boric compound (e.g. borone trifluoride-ethyl etherate, etc.) may be added to the reaction system.

[Reaction Scheme-20]

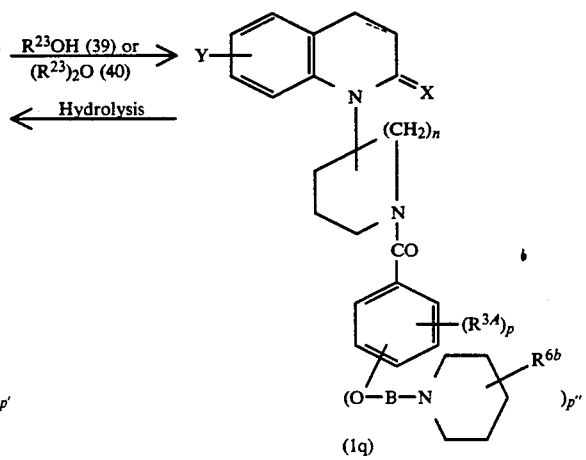

wherein X, Y, R³⁴, B, p, p′, p″, and the bond between 3- and 4-positions of the carbostyril nucleus are the same as defined above, and R⁶ᵃ is amino, R⁶ᵇ is an amino substituted by a lower alkanoyl having optionally 1 to 3 halogen substituents, and R²³ is a lower alkanoyl having optionally to 3 halogen substituents.

The reaction of the compound (lp) and the compound (39) is carried out under the same conditions as in the reaction of the compound (1d) and the compound (7) in the above Reaction Scheme-5.

The reaction of the compound (lp) and the compound (40) is carried out without solvent or in an appropriate solvent in the presence or absence, preferably presence, of a basic compound. The solvent includes, for example, the above-mentioned aromatic hydrocarbons, lower alcohols (e.g. methanol, ethanol, propanol, etc.), dimethylformamide, dimethylsulfoxide, and further halogenated hydrocarbons (e.g. chloroform, methylene chloride, etc.), acetone, pyridine, and the like. The basic compound includes, for example, tertiary amines (e.g. triethylamine, pyridine, etc.), sodium hydroxide, potassium hydroxide, sodium hydride, and the like. The above reaction may also be carried out in a solvent (e.g. acetic acid, etc.) in the presence of a mineral acid (e.g. sulfuric acid, etc.). The compound (40) is usually used in an equimolar amount or more, preferably about 1 to 10 moles, to 1 mole of the compound (lp). The above reaction is usually carried out at a temperature of about 0° to 200° C., preferably about 0° to 150° C., for about 0.5 to 15 hours.

The hydrolysis of the compound (1q) can be carried out in an appropriate solvent or without solvent in the presence of an acid or a basic compound. The solvent includes, for example, water, lower alcohols (e.g. methanol, ethanol, isopropanol, etc.), ketones (e.g. acetone, methyl ethyl ketone, etc.), ethers (e.g. dioxane, tetrahydrofuran, ethylene glycol dimethyl ether, etc.), fatty acids (e.g. acetic acid, formic acid, etc.), or a mixture of these solvents. The acid includes, for example, mineral acids (e.g. hydrochloric acid, sulfuric acid, hydrobromic acid, etc.) and organic acids (e.g. formic acid, acetic acid, aromatic sulfonic acids, etc.). The basic compound includes, for example, metal carbonates (e.g. sodium carbonate, potassium carbonate, etc.), metal hydoxides (e.g. sodium hydroxide, potassium hydroxide, calcium hydroxide, etc.), and the like. The reaction is usually carried out at a temperature of from room temperature to about 200° C., preferably from room temperature to about 150° C., for about 0.5 to 25 hours.

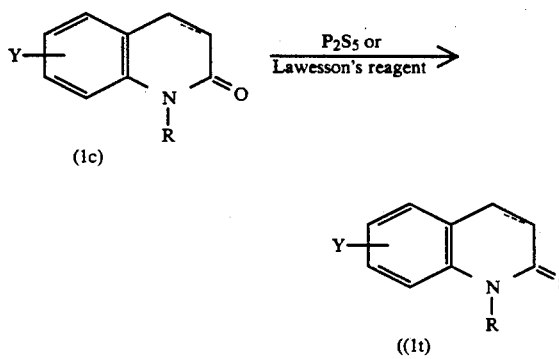

[Reaction Scheme-21]

wherein R, Y and the bond between 3- and 4-positions of the carbostyril nucleus are the same as defined above.

The reaction of the compound (1c) and phosphorus pentasulfide or Lawesson's reagent (as mentioned in Reference Example 1 hereinafter) is usually carried out in an inert solvent such as aromatic hydrocarbons (e.g. benzene, toluene, xylene, chlorobenzene, etc.), ethers (e.g. diethyl ether, tetrahydrofuran, dioxane, etc.), halogenated hydrocarbons (e.g. methylene chloride, chloroform, etc.), dimethylsulfoxide, hexamethylphosphoric triamide, and the like. The phosphorus pentasulfide or Lawesson's reagent is usually used in an amount of 0.2 mole to large excess amount, preferably 0.4 to 2 moles, to 1 mole of the compound (1c). The reaction is usually carried out at a temperature of from room temperature to 200° C., preferably 50° to 150° C., for 0.5 to 50 hours. compound (1h) or (1h') with a compound of the formula:

The starting compounds (1d), (1f), (1j), (11), (33), (35) and (37) can readily be prepared by various processes as shown in the above Reaction Schemes-1 to -5 by using appropriate starting materials.

In the case of the compounds of the formula (1) wherein $R^3$ is thiomorpholino or 1-oxothiomorpholino; or a pyrrolidinyl-substituted lower alkylthio or a pyrrolidinyl-substituted lower alkylsulfinyl can be converted into the corresponding compounds of the formula (1) wherein $R^3$ is 1-oxo- or 1,1-dioxothiomopholino or 1,1-dioxothiomorpholino; or a pyrrolidinyl-substituted lower alkyl-sulfinyl or -sulfonyl, or a pyrrolidinyl-substituted lower alkylsulfonyl, respectively by oxidation thereof.

The above oxidation reaction is carried out in an appropriate solvent in the presence of an oxidizing agent. The solvent includes, for example, water, organic acids (e.g. formic acid, acetic acid, trifluoroacetic acid, etc.), alcohols (e.g. methanol, ethanol, etc.), halogenated hydrocarbons (e.g. chloroform, dichloromethane, etc.), or a mixture of these solvents. The oxidizing agent includes, for example, peracids (e.g. performic acid, peracetic acid, trifluoro-peracetic acid, perbenzoic acid, m-chloroperbenzoic acid, o-carboxy-perbenzoic acid, etc.), hydrogen peroxide, sodium metaperiodate, dichromic acid, dichromates (e.g. sodium dichromate, potassium dichromate, etc.), permanganic acid, permanganates (e.g. potassium permanganate, sodium permanganate, etc.), lead salts (e.g. lead tetraacetate, etc.), and the like. The oxidizing agent is usually used in an amount of at least 1 mole, preferably 1 to 2 moles, to 1 mole of the starting compound. In case of converting thiomorpholino into 1,1-dioxothiomorpholino or converting pyrrolidinyl-substituted lower alkylthio into pyrrolidinyl-substituted lower alkylsulfonyl, the oxiding agent is usually used in an amount of at least two moles, preferably 2 to 4 moles, to 1 mole of the starting compound. The above reaction is usually carried out at a temperature of about −40° C. to about 40° C., preferably from about −40° C. to room temperature, for about 10 minutes to about 10 hours.

In the case of the compounds of the formula (1) wherein $R^3$ is a phenylthio having at least one nitro substituent, the compounds can be subjected to a reduction reaction to convert into the corresponding compounds wherein $R^3$ is a phenylthio having at least one amino substituent.

The reduction reaction can be carried out, for example, (1) by reducing them in an appropriate solvent with a catalytic reducing agent, or (2) by reducing them in an appropriate inert solvent with a reducing agent, such as a combination of a metal or metal salt and an acid, or a metal or metal salt and an alkali metal hydroxide, sulfide, ammonium salt, and the like.

In the case of reduction using a catalytic reducing agent (1), the solvent includes, for example, water, acetic acid, alcohols (e.g. methanol, ethanol, isopropanol, etc.), hydrocarbons (e.g. hexane, cyclohexane, etc.), ethers (e.g. dioxane, tetrahydrofuran, diethyl ether, diethylene glycol dimethyl ether, etc.), esters (e.g. ethyl acetate, methyl acetate, etc.), aprotic polar solvent (e.g. N,N-dimethylformamide, etc.), and the like. The catalytic reducing agent includes, for example, palladium, palladium black, palladium-carbon, platinum, platinum oxide, copper chromite, Raney nickel, and the like. The catalyst is usually used in an amount of 0.02 to 1 part by weight to 1 part by weight of the starting compound. The reaction is usually carried out at a temperature of about −20° C. to about 150° C., preferably from about 0° C. to about 100° C., under a hydrogen pressure of 1 to 10 atm., for about 0.5 to 10 hours.

In the case of the reduction (2), the reducing agent includes a combination of iron, zinc, tin or stannous chloride with a mineral acid (e.g. hydrochloric acid, sulfuric acid, etc.), or of iron, ferrous sulfate, zinc or tin with an alkali metal hydroxide (e.g. sodium hydroxide, etc.), a sulfide (e.g. ammonium sulfide, etc.), aqueous ammonia, or an ammonium salt (e.g. ammonium chloride, etc.). The inert solvent includes, for example, water, acetic acid, methanol, ethanol, dioxane, and the like. The conditions of the reduction reaction are determined depending on the kinds of the reducing agent, for example, in case of a combination of stannous chloride and hydrochloric acid, it is advantageously carried out at a temperature of about 0° C. to room temperature for about 0.5 to 10 hours. The reducing agent is usually used in an amount of at least 1 mole, preferably 1 to 5 moles, to 1 mole of the starting compound.

In case of the compounds of the formula (i) wherein $R^3$ is a heterocyclic group where the substituent on at least one nitrogen atom is hydrogen atom, the compounds can be converted into the corresponding compounds wherein $R^3$ is a heterocyclic group where the substituent on at least one nitrogen is a lower alkyl by reacting them with a compound of the formula:

wherein $R^{18}$ and $X^1$ are the same as defined above, or a compound of the formula:

wherein $R^{14}$ and $R^{15}$ are the same as defined above, under the same conditions as in the reaction of the compound (1f) and the compound (7b) in the above Reaction Scheme-6A or in the reaction of the compound (1h) and the compound (8) in the above Reaction Scheme-6B.

Among the active compounds (1) of this invention, the compounds having an acidic group can easily be converted into salts by treating with a pharmaceutically acceptable basic compound. The basic compound includes, for example, metal hydroxides such as sodium hydroxide, potassium hydroxide, lithium hydroxide, calcium hydroxide, etc., alkali metal carbonates or hydrogen carbonates such as sodium carbonate, sodium hydrogen carbonate, etc., alkali metal alcoholates such as sodium methylate, potassium ethylate, etc. Besides, among the active compounds (1) of this invention, the compounds having a basic group can easily be converted into acid addition salts thereof by treating with a pharmaceutically acceptable acid. The acid includes, for example, inorganic acids such as sulfuric acid, nitric acid, hydrochloric acid, hydrobromic acid, etc., and organic acids such as acetic acid, p-toluenesulfonic acid, ethanesulfonic acid, oxalic acid, maleic acid, citric acid, succinic acid, benzoic acid, etc. Besides, the compounds (1) of this invention include stereoisomers and optical isomers, and these isomers are also useful as the active ingredient in this invention.

The compounds of this invention thus obtained can easily be isolated and purified by conventional isolation methods. The isolation methods are, for example, distillation method, recrystallization method, column chromatography, ion exchange chromatography, gel chromatography, affinity chromtography, preparative thin layer chromatography, extraction with a solvent, and the like.

The compounds and their salts of this invention are useful as a vasopressin antagonist and are used in the form of a conventional pharmaceutical preparation. The preparation is prepared by using conventional diluents or carriers such as fillers, thickening agents, binders, wetting agents, disintegrators, surfactants, lubricants, and the like. The pharmaceutical preparations may be selected from various forms in accordance with the desired utilities, and the representative forms are tablets, pills, powders, solutions, suspensions, emulsions, granules, capsules, suppositories, injections (solutions, suspensions, etc.), and the like. In order to form in tablets, there are used carriers such as vehicles (e.g. lactose, white sugar, sodium chloride, glucose, urea, starches, calcium carbonate, kaolin, crystalline cellulose, silicic acid, etc.), binders (e.g. water, ethanol, propanol, simple syrup, glucose solution, starch solution, gelatin solution, carboxymethyl cellulose, shellac, methyl cellulose, potassium phosphate, polyvinylpyrrolidone, etc.), disintegrators (e.g. dry starch, sodium arginate, agar powder, laminaran powder, sodium hydrogen carbonate, calcium carbonate, polyoxyethylene sorbitan fatty acid esters, sodium laurylsulfate, stearic monoglyceride, starches, lactose, etc.), disintegration inhibitors (e.g. white sugar, stearin, cacao butter, hydrogenated oils, etc.), absorption promoters (e.g. quaternary ammonium base, sodium laurylsulfate, etc.), wetting agents (e.g. glycerin, starches, etc.), adsorbents (e.g. starches, lactose, kaolin, bentonite, colloidal silicates, etc.), lubricants (e.g. purified talc, stearates, boric acid powder, polyethylene glycol, etc.), and the like. Moreover, the tablets may also be in the form of a conventional coated tablet, such as sugar-coated tablets, gelatin-coated tablets, enteric-coated tablets, film coating tablets, or double or multiple layer tablets. In the preparation of pills, the carriers include vehicles (e.g. glucose, lactose, starches, cacao butter, hydrogenated vegetable oils, kaolin, talc, etc.), binders (e.g. gum arabic powder, tragacanth powder, gelatin, ethanol, etc.), disintegrators (e.g. laminaran, agar, etc.), and the like. In the preparation of suppositories, the carriers include, for example, polyethylene glycol, cacao butter, higher alcohols, higher alcohol esters, gelatin, semi-synthetic glycerides, and the like. Capsules can be prepared by charging a mixture of the compound of this invention with the above carriers into hard gelatin capsules or soft capsules in a usual manner. In the preparation of injections, the solutions, emulsions or suspendions are sterilized and are preferably made isotonic with the blood. In the preparation of these solutions, emulsions and suspensions, there are used conventional diluents, such as water, ethyl alcohol, macrogol, propylene glycol, ethoxylated isostearyl alcohol, polyoxylated isostearyl alcohol, polyoxyethylene sorbitan fatty acid esters, and the like. In this case, the pharmaceutical preparations may also be incorporated with sodium chloride, glucose, or glycerin in an amount sufficient to make them isotonic, and may also be incorporated with conventional solubilizers, buffers, anesthetizing agents. Besides, the pharmaceutical preparations may optionally be incorporated with coloring agents, preservatives, perfumes, flavors, sweeting agents, and other medicaments, if required.

The amount of the active compound of this invention (active ingredient) to be incorporated into the anti-vasopressin preparations is not specified but may be selected from a broad range, but usually, it is preferably in the range of 1 to 70% by weight, more preferably 5 to 50% by weight.

The anti-vasopressin preparation of this invention may be administered in any method, and suitable method for administration may be determined in accordance with various forms of preparation, ages, sexes and other conditions of the patients, the degree of severity of diseases, and the like. For instance, tablets, pills, solutions, suspensions, emulsions, granules and capsules are administered orally. The injections are intravenously administered alone or together with a conventional auxiliary liquid (e.g. glucose, amino acid solutions), and further are optionally administered alone in intramuscular, intracutaneous, subcutaneous, or intraperitoneal route, if required. Suppositories are administered in intrarectal route.

The dosage of the anti-vasopressin agent of this invention may be selected in accordance with the usage, ages, sexes and other conditions of the patients, the degree of severity of the diseases, and the like, but is usually in the range of about 0.6 to 50 mg of the active compound of this invention per 1 kg of body weight of the patient per day. The active compound is preferably contained in an amount of 10 to 1000 mg per the dosage unit.

EXAMPLES

The present invention is illustrated by the following Preparations of anti-vasopressin agent, Reference Examples of processes for preparing the starting compounds to be used for preparing the active compounds, Examples of processes for preparing the active compounds, and Experiments of the activities of the active compounds of this invention.

Preparation 1

Film coated tablets are prepared from the following components.

| Component | Amount |
| --- | --- |
| 1-{1-[4-(3-Hydroxy-4-allylaminobutoxy)-benzoyl]-4-piperidinyl}-3,4-dihydrocarbostyril | 150 g |
| Avicel (tradename of microcrystalline cellulose, manufactured by Asahi Chemical Industry Co., Ltd., Japan) | 40 g |
| Corn starch | 30 g |
| Magnesium stearate | 2 g |
| Hydroxypropyl methylcellulose | 10 g |
| Polyethylene glycol-6000 | 3 g |
| Castor oil | 40 g |
| Ethanol | 40 g |

The active component of this invention, Avicel, corn starch and magnesium stearate are mixed and kneaded and the mixture is tabletted using a conventional pounder (R 10 mm) for sugar coating. The tablets thus obtained are coated with a film coating agent consisting of hydroxypropyl methylcellulose, polyethylene glycol-6000, castor oil and ethanol to give film coated tablets.

Preparation 2

Tablets are prepared from the following components.

| Components | Amount |
| --- | --- |
| 1-[1-{4-[(4-Amino-1-piperdinyl)pentyloxy]-benzoyl}-4-piperdinyl]-3,4-dihydrocarbostyril | 150 g |
| Citric acid | 1.0 g |
| Lactose | 33.5 g |
| Dicalcium phosphate | 70.0 g |
| Pullonic F-68 | 30.0 g |
| Sodium laurylsulfate | 15.0 g |
| Polyvinylpyrrolidone | 15.0 g |
| Polyethylene glycol (Carbowax 1500) | 4.5 g |
| Polyethylene glycol (Carbowax 6000) | 45.0 g |
| Corn starch | 30.0 g |
| Dry sodium stearate | 3.0 g |
| Dry magnesium stearate | 3.0 g |
| Ethanol | q.s. |

The active compound of this invention, citric acid, lactose, dicalcium phosphate, Pullonic F-68 and sodium laurylstearate are mixed. The mixture is screened with No. 60 screen and is granulated with an alcohol solution containing polyvinylpyrrolidone, carbowax 1500 and 6000. If required, an alcohol is added thereto so that the powder mixture is made a paste-like mass. Corn starch is added to the mixture and the mixture is continuously mixed to form uniform particles. The resulting particles are passed through No. 10 screen and entered into a tray and then dried in an oven at 100° C., for 12 to 14 hours. The dried particles are screened with No. 16 screen and thereto are added dry sodium laurylsulfate and dry magnesium stearate, and the mixture is tabletted to form the desired shape.

The core tablets thus prepared are vanished and dusted with talc in order to guard from wetting. Undercoating is applied to the core tablets. In order to administer the tablets orally, the core tablets are vanished several times. In order to give round shape and smooth surface to the tablets, further undercoating and coating with lubricant are applied thereto. The tablets are further coated with a coloring coating material until the desired colored tablets are obtained. After drying, the coated tablets are polished to obtain the desired tablets having uniform gloss.

Preparation 3

An injection preparation is prepared from the following components.

| Components | Amount |
| --- | --- |
| 1-{1-[4-(5-Methylaminocarbonyloxy-6-dimethylaminohexyloxy)benzoyl)-4-piperidinyl]-3,4-dihydrocarbostyril | 5 g |
| Polyethylene glycol (molecular weight: 4000) | 0.3 g |
| Sodium chloride | 0.9 g |
| Polyoxyethylene sorbitan monooleate | 0.4 g |
| Sodium metabisulfate | 0.1 g |
| Methyl-paraben | 0.18 g |
| Propyl-paraben | 0.02 g |
| Distilled water for injection | 10.0 ml |

The above parabens, sodium metabisulfite and sodium chloride are dissolved in distilled water of half volume of the above with stirring at 80° C. The solution thus obtained is cooled to 40° C., and the active compound of this invention and further polyethylene glycol and polyoxyethylene sorbitan monooleate are dissolved in the above solution. To the solution is added distilled water for injection to adjust to the desired volume, and the solution is sterilized by filtering with an appropriate filter paper to give an injection preparation.

REFERENCE EXAMPLE 1

1-(4-Piperidinyl)-3,4-dihydrocarbostyril hydrochloride (5 g) and a Lawesson's Reagent *) (3.8 g) are dispersed in toluene (20 ml), and the mixture is refluxed for 40 hours. To the reaction mixture is added water, and the mixture is acidified with hydrochloric acid, and the organic layer is separated. The aqueous layer is basified with sodium hydroxide, extracted with chloroform, dried over sodium carbonate and recrystallized from n-hexane. The crystal is collected by filtration, and crystallized from dichloromethane/n-hexane to give 1-(4-piperidinyl)-3,4-dihydrothiocarbostyril (4.1 g) as pale yellow powder, m.p. 94°–97° C.

*) Lawesson's Reagent:

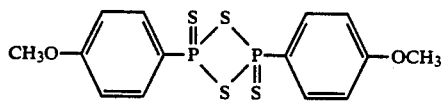

EXAMPLE 1

1-(4-Piperidinyl)-3,4-dihydrothiocarbostyril (1.1 g), 4-ethoxy-2-methoxybenzoic acid (1.05 g) and bisoxooxazodinylphosphinyl chloride (1.4 g) are dissolved in dichloromethane (30 ml) and thereto is added triethylamine (1.4 ml), and the mixture is stirred at room temperature overnight. Water is added to the reaction mixture, and the mixture is extracted with chloroform, dried over sodium carbonate, and purified by silica gel column chromatography (eluent; ethyl acetate:n-hexane=1:1) to give 1-[1-(2-methoxy-4-ethoxybenzoyl)-4-piperidinyl]-3,4-dihydrothiocarbostyril (0.9 g) as pale yellow amorphous.

$^1$H-NMR (CDCl$_3$) δ ppm; 1.42 (3H, t, J=7.0 Hz), 1.79–2,17 (2H, m), 2.26–2.59 (2H, m), 2.63–3.36 (6H, m), 3.59–3.64 (1H, m), 3.76–3.92 (3H, m), 4.04 (2H, q, J=7.0 Hz), 4.88–5.05 (1H, m), 5.92–6.13 (1H, m), 6.44–6.58 (2H, m), 7.06–7.45 (5H, m)

Using the suitable starting materials, the compounds of the following Table 1 are obtained in the same manner as in Example 1.

TABLE 1

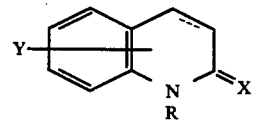

Example 2
Structure

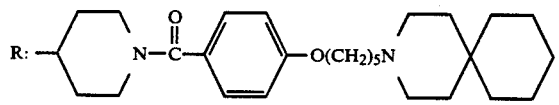

X: O    Y: H
Bond between 3- and 4-positions
of the carbosytril nucleus: Single bond Crystalline form: Colorless oil
Form: Free
NMR: 1)

Example 3
Structure

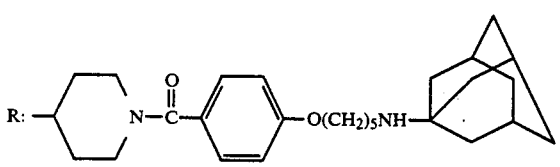

X: O    Y: H
Bond between 3- and 4-positions
of the carbosytril nucleus: Single bond Crystalline form: White powder
Recrystallization solvent: Ethanol/water
Melting point: 125–129° C.
Form: Hydrochloride

Example 4
Structure

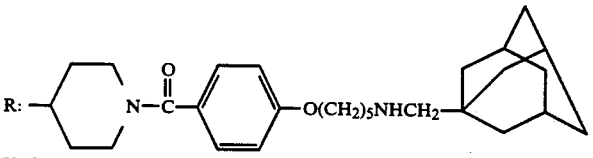

X: O    Y: H
Bond between 3- and 4-positions
of the carbosytril nucleus: Single bond Crystalline form: Colorless oil
Form: Free
NMR: 2)

Example 5
Structure

TABLE 1-continued

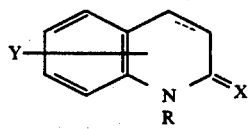

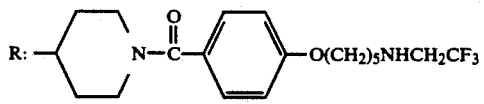

X: O  Y: H
Bond between 3- and 4-positions
of the carbosytril nucleus: Single bond Crystalline form: Colorless oil
Form: Free
NMR: 3)

Example 6
Structure

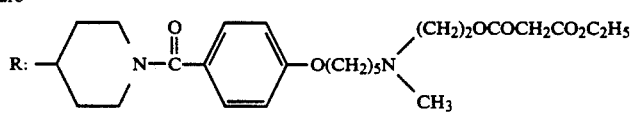

X: O  Y: H
Bond between 3- and 4-positions
of the carbosytril nucleus: Single bond Crystalline form: Colorless oil
Form: Free
NMR: 4)

Example 7
Structure

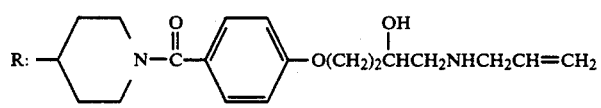

X: O  Y:H
Bond between 3- and 4-positions
of the carbosytril nucleus: Single bond Crystalline form: Colorless oil
Form: Free
NMR: 5)

Example 8
Structure

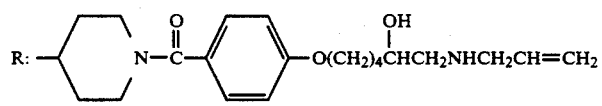

X: O  Y: H
Bond between 3- and 4-positions
of the carbosytril nucleus: Single bond Crystalline form: Colorless oil
Form: Free
NMR: 6)

Example 9
Structure

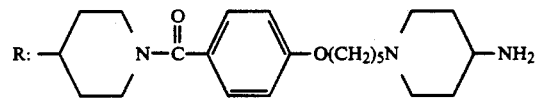

X: O  Y: H
Bond between 3- and 4-positions
of the carbosytril nucleus: Single bond Crystalline form: Colorless oil
Form: Free
NMR: 7)

Example 10

TABLE 1-continued

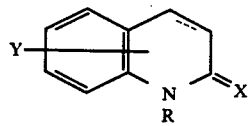

Structure

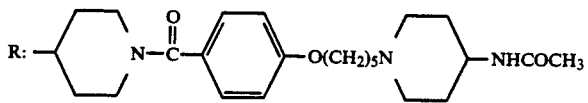

X: O  Y: H
Bond between 3- and 4-positions
of the carbosytril nucleus: Single bond Crystalline form: Colorless oil
Form: Free
NMR: 8)

Example 11
Structure

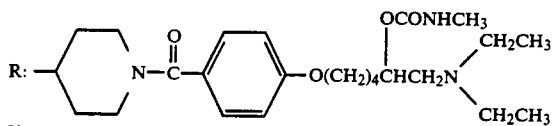

X: O  Y: H
Bond between 3- and 4-positions
of the carbosytril nucleus: Single bond Crystalline form: Colorless oil
Form: Free
NMR: 9)

Example 12
Structure

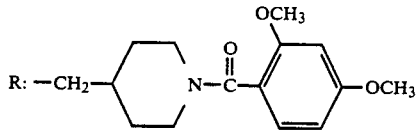

X: O  Y: H
Bond between 3- and 4-positions
of the carbosytril nucleus: Single bond Crystalline form: Colorless amorphous
Form: Free
NMR: 10)

Example 13
Structure

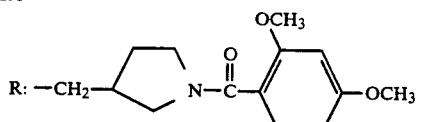

X: O  Y: H
Bond between 3- and 4-positions
of the carbosytril nucleus: Single bond Crystalline form: Colorless amorphous
Form: Free
NMR: 11)

Example 14
Structure

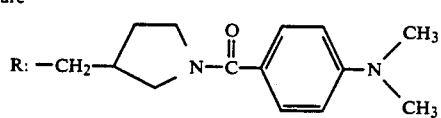

X: O  Y: H
Bond between 3- and 4-positions
of the carbosytril nucleus: Single bond Crystalline form: Colorless amorphous TABLE 1-continued

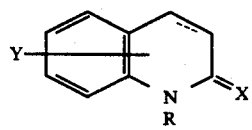

Form: Free
NMR: 12)

Example 15
Structure

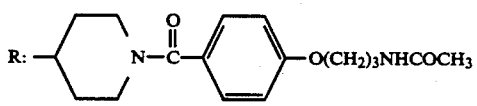

X: S  Y: H
Bond between 3- and 4-positions
of the carbosytril nucleus: Single bond Crystalline form: Pale yellow powder
Recrystallization solvent: Dichloromethane/n-hexane
Melting point: 182–183° C.
Form: Free Example 16
Structure

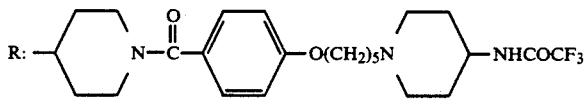

X: O  X: H
Bond between 3- and 4-positions
of the carbosytril nucleus: Single bond Crystalline form: Colorless oil
Form: Free
NMR: 13)

Example 17
Structure

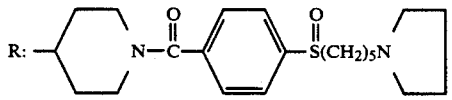

X: O  Y: H
Bond between 3- and 4-positions
of the carbosytril nucleus: Single bond Crystalline form: White amorphous
Form: Free
NMR: 14)

Example 18
Structure

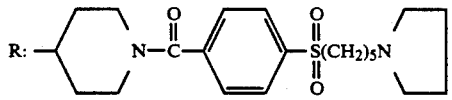

X: O  Y: H
Bond between 3- and 4-positions
of the carbosytril nucleus: Single bond Crystalline form: White amorphous
Form: Free
NMR: 15)

Example 19
Structure

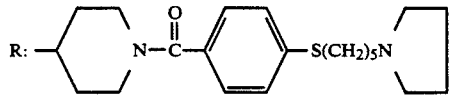

X: O  Y: H
Bond between 3- and 4-positions
of the carbosytril nucleus: Single bond TABLE 1-continued

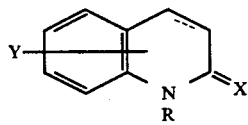

Crystalline form: White amorphous
Form: Hydrochloride
NMR: 16)

Example 20
Structure

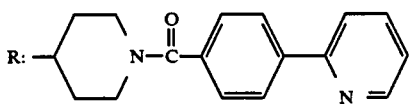

X: O  Y: H
Bond between 3- and 4-positions
of the carbosytril nucleus: Single bond Crystalline form: Colorless prisms
Recrystallization solvent: Methanol
Melting point: 198–200° C.
Form: Free Example 21
Structure

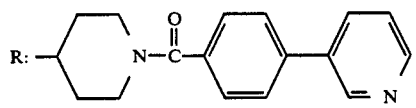

X: O  Y: H
Bond between 3- and 4-positions
of the carbosytril nucleus: Single bond Crystalline form: Colorless prisms
Recrystallization solvent: Ethyl acetate
Melting point: 151–153° C.
Form: Free Example 22
Structure

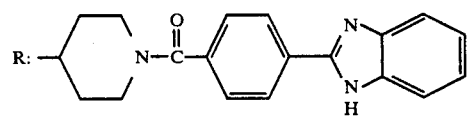

X: O  Y: H
Bond between 3- and 4-positions
of the carbosytril nucleus: Single bond Crystalline form: Colorless needles
Recrystallization solvent: Methanol
Melting point: 240–243° C.
Form: Free Example 23
Structure

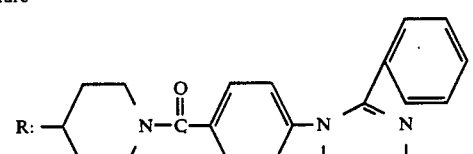

X: O  Y: H
Bond between 3- and 4-positions
of the carbosytril nucleus: Single bond Crystalline form: White powder
Recrystallization solvent: Methanol
NMR: 17)
Melting point: 107–113° C.
Form: Free TABLE 1-continued

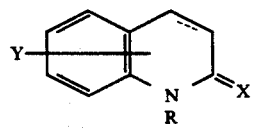

Example 24

Structure

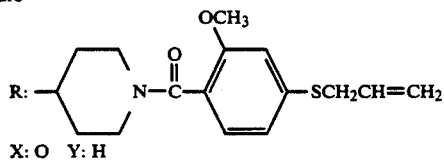

X: O  Y: H
Bond between 3- and 4-positions
of the carbosytril nucleus: Single bond Crystalline form: White amorphous
Form: Free
NMR: 18)

Example 25

Structure

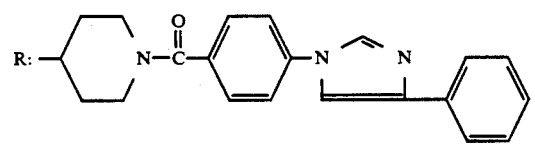

X: O  Y: H
Bond between 3- and 4-positions
of the carbosytril nucleus: Single bond Crystalline form: Colorless scales
Recrystallization solvent: Ethyl acetate
Melting point: 203–206° C.
Form: Free Example 26

Structure

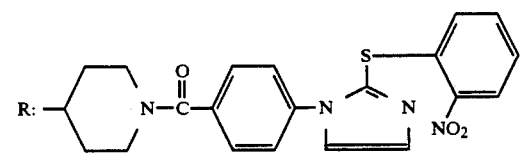

X: O  Y: H
Bond between 3- and 4-positions
of the carbosytril nucleus: Single bond Crystalline form: Pale yellow powder
Recrystallization solvent: Methanol/chloroform
Melting point: 224–225.5° C.
Form: Free Example 27

Structure

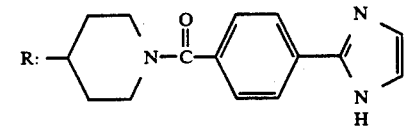

X: O  Y: H
Bond between 3- and 4-positions
of the carbosytril nucleus: Single bond Crystalline form: White powder
Form: Free
NMR: 19)

Example 28

Structure

TABLE 1-continued

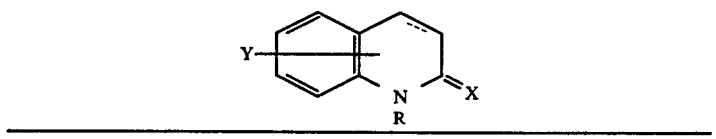

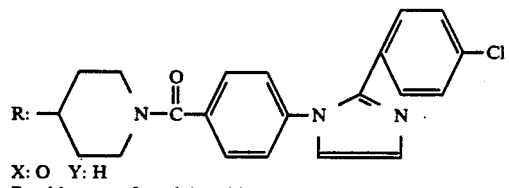

X: O  Y: H
Bond between 3- and 4-positions
of the carbosytril nucleus: Single bond Crystalline form: Colorless prisms
Recrystallization solvent: Methanol
NMR: 20)
Melting point: Over 100° C. (decomposed)
Form: Free Example 29
Structure

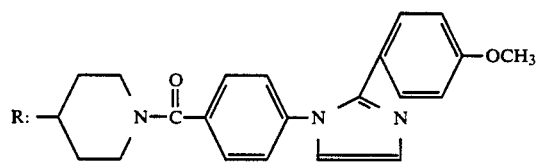

X: O  Y: H
Bond between 3- and 4-positions
of the carbosytril nucleus: Single bond Crystalline form: Colorless prisms
Recrystallization solvent: Methanol
Melting point: 122–124° C.
Form: Free Example 30
Structure

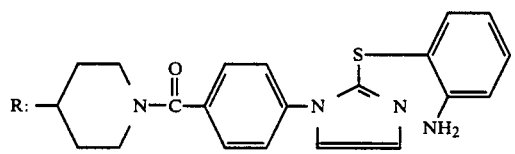

X: O  Y: H
Bond between 3- and 4-positions
of the carbosytril nucleus: Single bond Crystalline form: White powder
Form: Free
NMR: 21)

Example 31
Structure

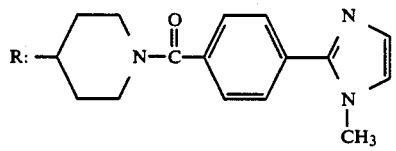

X: O  Y: H
Bond between 3- and 4-positions
of the carbosytril nucleus: Single bond Crystalline form: Colorless scales
Recrystallization solvent: Ethyl acetate
Melting point: 177–179° C.
Form: Free Example 32
Structure

TABLE 1-continued

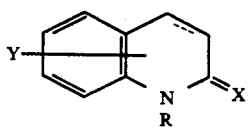

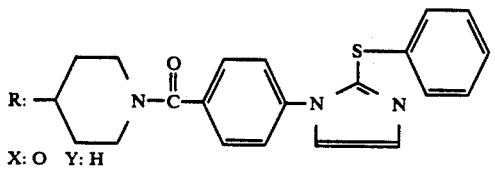

X: O  Y: H
Bond between 3- and 4-positions
of the carbosytril nucleus: Single bond Crystalline form: White powder
Form: Free
NMR: 22)

Example 33
Structure

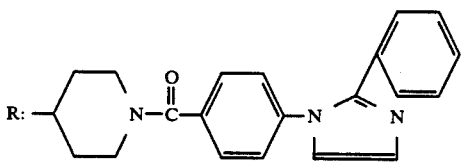

X: O  Y: H
Bond between 3- and 4-positions
of the carbosytril nucleus: Double bond Crystalline form: Slightly yellow prisms
Recrystallization solvent: Methanol
Melting point: 113–116° C.
Form: Free 1) $^1$H-NMR (CDCl$_3$) δ ppm: 1.23–1.93 (22H, m), 2.35–3.12 (14H, m), 3.86–4.96 (3H, m), 3.98 (2H, t, J=6.4 Hz), 6.82–6.93 (2H, m), 6.96–7.32 (4H, m), 7.35–7.48 (2H, m)

2) $^1$H-NMR (CDCl$_3$) δ ppm: 1.42–2.03 (23H, m), 2.27 (2H, s), 2.50–3.13 (10H, m), 3.87–4.40 (3H, m), 3.98 (2H, t, J=6.4 Hz), 6.85–6.95 (2H, m), 6.97–7.32 (4H, m), 7.33–7.48 (2H, m)

3) $^1$H-NMR (CDCl$_3$) δ ppm: 1.40–1.97 (9H, m), 2.53–3.16 (10H, m), 3.18 (2H, q, J=9.5 Hz), 3.83–4.98 (3H, m), 3.99 (2H, t, J=6.3 Hz), 6.82–6.95 (2H, m), 6.97–7.32 (4H, m), 7.35–7.48 (2H, m) 4) $^1$H-NMR (CDCl$_3$) δ ppm: 1.28 (3H, t, J=7.1 Hz), 1.38–1.93 (8H, m), 2.28 (3H, s), 2.35–3.10 (12H, m), 3.39 (2H, s), 3.82–4.96 (3H, m), 3.98 (2H, t, J=6.4 Hz), 4.19 (2H, q, J=7.1 Hz), 4.25 (2H, t, J=6.5 Hz), 6.83–7.46 (8H, m)

5) $^1$H-NMR (CDCl$_3$) δ ppm: 1.65–2.08 (3H, m), 2.52–3.13 (10H, m), 3.27–3.56 (5H, m), 3.83–4.98 (6H, m), 5.13–5.31 (2H, m), 5.81–6.02 (1H, m), 6.83–7.46 (8H, m)

6) $^1$H-NMR (CDCl$_3$) δ ppm: 1.40–1.92 (8H, m), 2.43–3.12 (12H, m), 3.21–3.42 (2H, m), 3.61–3.76 (1H, m), 3.82–3.94 (3H, m), 3.99 (2H, t, J=6.3 Hz), 5.10–5.28 (2H, m), 5.80–6.01 (1H, m), 6.85–7.48 (8H, m)

7) $^1$H-NMR (CDCl$_3$) δ ppm: 1.30–1.68 (6H, m), 1.69–2.21 (8H, m), 2.15–2.40 (4H, m), 2.48–3.12 (11H, m), 3.87–5.00 (3H, m), 3.98 (2H, t, J=6.4 Hz), 6.82–6.93 (2H, m), 6.97–7.31 (4H, m), 7.35–7.48 (2H, m)

8) $^1$H-NMR (CDCl$_3$) δ ppm: 1.41–1.93 (12H, m), 1.97 (3H, m), 2.08–2.26 (2H, m), 2.83–3.29 (12H, m), 3.70–5.08 (4H, m), 3.99 (2H, t, J=6.3 Hz), 5.60–5.73 (1H, m), 6.83–6.92 (2H, m), 6.95–7.31 (4H, m), 7.37–7.46 (2H, m)

9) $^1$H-NMR (CDCl$_3$) δ ppm: 1.00 (6H, t, J=7.1 Hz) 1.45–1.97 (8H, m), 2.40–3.10 (18H, m), 3.90–5.03 (4H, m), 3.99 (2H, t, J=6.2 Hz), 6.82–6.95 (2H, m), 6.98–7.33(4H, m), 7.46–7.50 (2H, m)

10) $^1$H-NMR (CDCl$_3$) δ ppm: 1.05–2.10 (4H, m), 2.55–3.00 (7H, m), 3.40–4.15 (9H, m), 4.65–4.80 (1H, m), 6.35–6.5 (2H, m), 6.90–7.30 (5H, m)

11) $^1$H-NMR (CDCl$_3$) δ ppm: 1.65–2.15 (2H, m), 2.65–3.00 (5H, m), 3.05–4.40 (12H, m), 6.40–6.55 (2H, m), 6.90–7.10 (2H, m), 7.10–7.30 (3H, m)

12) $^1$H-NMR (CDCl$_3$) δ ppm: 1.65–2.15 (2H, m), 2.55–3.05 (5H, m), 2.99 (6H, s), 3.35–4.50 (6H, m), 6.65 (2H, d, J=8.9 Hz), 6.90–7.10 (2H, m), 7.10–7.30 (2H, m), 2.48 (2H, d, J=8.9 Hz)

13) $^1$H-NMR (CDCl$_3$) δ ppm: 1.37–1.63 (6H, m), 1.68–2.17 (8H, m), 2.30–2.41 (2H, m), 2.52–3.10 (10H, m), 3.70–5.04 (4H, m), 4.00 (2H, t, J=6.4 Hz), 6.35–6.50 (1H, m), 6,85–6.95 (2H, m), 6.98–7.31 (4H, m), 7.37–7.47 (2H, m)

14) $^1$H-NMR (CDCl$_3$) δ ppm: 1.3–2.2 (12H, m), 2.3–3.3 (16H, m), 3.6–4.0 (1H, m), 4.25–4.45 (1H, m), 4.7–5.1 (1H, m), 7.0–7.35 (4H, m), 7.62 (2H, d, J=8.5 Hz), 7.67 (2H, d, J=8.5 Hz)

15) $^1$H-NMR (CDCl$_3$) δ ppm: 1.2–2.1 (12H, m), 2.3–3.25 (16H, m), 3.6–3.85 (1H, m), 4.2–4.4 (1H, m), 4.8–5.1 (1H, m), 6.95–7.15 (2H, m), 7.15–7.35 (2H, m), 7.65 (2H, d, J=8.4 Hz), 7.96 (2H, d, J=8.4 Hz)

16) $^1$H-NMR (DMSO-d$_6$) δ ppm: 1.3–2.1 (12H, m), 2.3–2.7 (5H, m), 2.7–3.2 (10H, m), 3.4–3.9 (2H, m), 4.1–4.8 (2H, m), 6.95–7.1 (1H, m), 7.2–7.5 (7H, m), 10.37 (1H, brs)

17) $^1$H-NMR (DMSO-d$_6$) δ ppm: 1.5–2.0 (2H, m), 2.3–3.3 (8H, m), 3.4–3.8 (1H, m), 4.2–4.45 (1H, m), 4.45–4.8 (1H, m), 6.95–7.1 (1H, m), 7.2–7.4 (11H, m), 7.4–7.6 (3H, m)

18) $^1$H-NMR (CDCl$_3$) δ ppm: 1.6–1.9 (2H, m), 2.5–3.2 (8H, m), 3.5–3.7 (3H, m), 3.75–3.95 (3H, m), 4.2–4.7 (1H, m), 4.85–5.05 (1H, m), 5.05–5.3 (2H,m), 5.8–6.05 (1H, m), 6.85–7.35 (7H, m)

19) $^1$H-NMR (CDCl$_3$) δ ppm: 1.6–2.1 (2H, m), 2.5–3.2 (8H, m), 3.7–4.1 (1H, m), 4.2–4.45 (1H, m), 4.6–5.2 (1H, m), 5.5–6.8 (1H, m), 6.95–7.3 (6H, m), 7.38 (2H, d, J=8.3 Hz), 7.85 (2H, d, J=8.3 Hz)

20) $^1$H-NMR (CDCl$_3$) δ ppm: 1.7–2.1 (2H, m), 2.5–3.4 (8H, m), 3.6–4.2 (1H, m), 4.2–4.5 (1H, m), 4.5–5.2 (1H, m), 7.0–7.4 (12H, m), 7.53 (2H, d, J=8.4 Hz)

21) $^1$H-NMR (CDCl$_3$) δ ppm: 1.7–2.1 (2H, m), 2.5–3.5 (10H, m), 3.7–4.2 (1H, m), 4.2–4.5 (1H, m), 4.6–5.2 (1H, m), 6.47 (1H, dt, J=1.2 Hz, 8.0 Hz), 7.62 (1H, dd, J=1.2 Hz, 8.0 Hz), 6.95 (1H, dd, J=1.2 Hz, 8.0 Hz), 7.0–7.3 (7H, m), 7.34 (2H, d, J=8.4 Hz), 7.54 (2H, d, J=8.4 Hz)

22) $^1$H-NMR (CDCl$_3$) δ ppm: 1.7–2.0 (2H, m), 2.5–3.2 (8H, m), 3.7–4.0 (1H, m), 4.25–4.45 (1H, m), 4.7–5.1 (1H, m), 7.0–7.4 (13H, m), 7.48 (2H, d, J=8.4 Hz)

EXAMPLE 34

1-[1-{4-[5-(4-Trifluoroacetylamino-1-piperidinyl-pentyloxy]benzoyl}-4-piperidinyl]-3,4-dihydrocarbostyril (1.8 g) is dissolved in methanol (40 ml), and thereto is added potassium carbonate (0.8 g). The mixture is stirred at room temperature overnight. The reaction solution is concentrated and thereto is added water. The mixture is extracted with chloroform, dried over sodium carbonate, and purified by silica gel column chromatography (eluent; dichloromethane: methanol=10:1) to give 1-[1-{4-[5-(4-amino-1-piperidinyl)pentyloxy]benzoyl}-4-piperidinyl]-3,4-dihydrocarbostyril (1 g) as colorless oil.

$^1$H-NMR (CDCl$_3$) δ ppm: 1.30–1.68 (6H, m), 1.69–2.12 (8H, m), 2.15–2.40 (4H, m), 2.48–3.12 (11H, m), 3.87–5.00 (3H, m), 3.98 (2H, t, J=6.4 Hz), 6.82–6.93 (2H, m) 6.97–7.31 (4H, m), 7.35–7.48 (2H, m)

EXAMPLE 35

1-[1-{4-[5-(4-Amino-1-piperidinyl)pentyloxy]benzoyl}-4-piperidinyl]-3,4-dihydrocarbostyril (0.6 g) and acetic anhydride (0.2 ml) are dissolved in dichloromethane (20 ml), and thereto are added triethylamine (0.56 ml) and 1,4-dimethylaminopyridine (20 mg), and the mixture is stirred at room temperature overnight. Water is added to the reaction mixture and the mixture is extracted with chloroform, dried over sodium carbonate, and purified by silica gel column chromatography (eluent; dichloromethane: methanol=20:1) to give 1-[1-{4-[5-(4-acetylamino-1-piperidinyl)pentyloxy]benzoyl}-4-piperidinyl]-3,4-dihydrocarbostytril (310 mg) as colorless oil.

$^1$H-NMR (CDCl$_3$) δ ppm: 1.41–1.93 (12H, m), 1.97 (3H, s), 2.08–2.26 (2H, m), 2.38–3.29 (12H, m), 3.70–5.08 (4H, m), 3.99 (2H, t, J=6.3 Hz), 5.60–5.73 (1H, m), 6.83–6.92 (2H, m), 6.95–7.31 (4H, m), 7.37–7.46 (2H, m)

Using the suitable starting materials, the compounds of the above Examples 1 and 14 are obtained in the same manner as in Example 35.

EXAMPLE 36

1-{1-[4-(6-Diethylamino-5-hydroxyhexyloxy)benzoyl]-4-piperidinyl}-3,4-dihydrocarbostyril (0.7 g) and methyl isocyanate (0.24 ml) are dissolved in acetonitril (20 ml), and thereto is added trifluroboran ethyl ether complex (0.35 ml) under ice-cooling, and the mixture is stirred at room temperature overnight. The reaction mixture is concentrated and purified by silica gel column chromatography (eluent; dichloromethane: methanol=20:1) to give 1-{1-[4-(6-diethylamino-5-methylaminocarbonyloxyhexyloxy)benzoyl]-4-piperidinyl}-3,4-dihydrocarbostyril (314 mg) as colorless oil.

$^1$H-NMR (CDCl$_3$) δ ppm: 1.00 (6H, t, J=7.1 Hz), 1.45–1.97 (8H, m), 2.40–3.10 (18H, m), 3.90–5.03 (4H, m), 3.99 (2H, t, J=6.2 Hz), 6.82–6.95 (2H, m), 6.98–7.33 (4H, m), 7.46–7.50 (2H, m)

EXAMPLE 37

1-{1-[4-5-[(N-Methyl-N-(2-hydroxyethyl)amino]-pentyloxy}benzoyl]-4-piperidinyl}-3,4-dihydrocarbostyril (0.9 g) and ethylmalonyl chloride (0.28 ml) are dissolved in dichloroethane (10 ml), and thereto is added diisopropylethylamine (0.48 ml) under ice-cooling, and the mixture is stirred at room temperature overnight. The reaction mixture is concentrated and purified by silica gel column chromatography (eluent; dichloromethane: methanol=20:1) to give 1-{1-[4-{5-[(N-methyl-N-(2-ethoxycarbonylacetyloxyethyl)amino]pentyloxy}benzoyl]-4-piperidinyl}-3,4-dihydrocarbostyril (0.28 g) as colorless oil.

$^1$H-NMR (CDCl$_3$) δ ppm: 1.28 (3H, t, J=7.1 Hz), 1.38–1.93 (8H, m), 2.28 (3H, s), 2.35–3.10 (12H, m), 3.39 (2H, s), 3.82–4.96 (3H, m), 3.98 (2H, t, J=6.4 Hz), 4.19 m)

EXAMPLE 38

1-{1-[4-(4-Oxiranylbutoxy)benzoyl]-4-piperidinyl}-3,4-dihydrocarbostyril (4.6 g) is dissolved in methanol (100 ml), and thereto is added allylamine (10 ml), and the mixture is stirred overnight. The reaction mixture is concentrated and purified by silica gel column chromatography (eluent; dichloromethane: methanol=10:1) to give 1-{1-[4-(5-hydroxy-6-allylaminohexyloxy)benzoyl]-4-piperidinyl}-3,4-dihydrocarbostyril (2.5 g) as colorless oil.

$^1$H-NMR (CDCl$_3$) δ ppm: 1.40–1.92 (8H, m), 2.43–3.12 (12H, m), 3.21–3.42 (2H, m), 3.61–3.76 (1H, m), 3.82–3.94 (3H, m), 3.99 (2H, t, J=6.3 Hz), 5.10–5.28 (2H, m), 5.80–6.01 (1H, m), 6.85–7.48 (8H, m)

Using the suitable starting materials, the compound of the above Example 6 is obtained in the same manner as in Example 38.

EXAMPLE 39

1-{1-[4-(5-Bromopentyloxy)benzoyl]-4-piperidinyl}-3,4-dihydrocarbostyril (2 g) and 4-trifluoroacetylaminopiperidine (2 g) are dissolved in dimethylformamide (40 ml), and thereto is added potassium carbonate (2 g) and the mixture is stirred overnight. The reaction mixture is poured into water, and the mixture is extracted with toluene/ethyl acetate (1:1), dried over magnesium sulfate, and purified by silica gel column chromatography (eluent; dichloromethane: methanol=50:1) to give 1-[1-{4-[5-(4-trifluoroacetylamino-1-piperidinyl)pentyloxy]benzoyl}-4-piperidinyl]-3,4-dihydrocarbostyril (2 g) as colorless oil.

¹H-NMR (CDCl₃) δ ppm: 1.37–1.63 (6H, m), 1.68–2.17 (8H, m), 2.30–2.41 (2H, m), 2.52–3.10 (10H, m), 3.70–5.04 (4H, m), 4.00 (2H, t, J=6.4 Hz), 6.35–6.50 (1H, m), 6.85–6.95 (2H, m), 6.98–7.31 (4H, m), 7.37–7.47 (2H, m)

Using the suitable starting materials, the compounds of the above Examples 2–10 and 15 are obtained in the same manner as in Example 39.

EXAMPLE 40

To the mixture of conc. hydrochloric acid (3.2 ml) and ethanol (2 ml) is added 1-[1-{4-[2-(2-nitrophenyl)thio-1-imidazolyl]benzoyl}-4-piperidinyl]-3,4-dihydrocarbostyril (2.0 g), and thereto is added dropwise a solution of stannous chloride dihydrate (2.7 g) in ethanol (4 ml) at a temperature below 25° C. with water-cooling, and the mixture is stirred at room temperature for two hours. The mixture is poured into ice-water and basified with aqueous sodium hydroxide solution, extracted with chloroform, washed with water, and dried over sodium sulfate. After concentrated under reduced pressure, the resulting residue is purified by silica gel column chromatography (eluent; chloroform: methanol=50:1–25:1), and further dissolved in methanol. The mixture is added dropwise with stirring into water (about 40 ml) and the resulting precipitates are collected by filtration and dried to give 1-[1-{4-[2-(2-aminophenyl)thio-1-imidazolyl]benzoyl}-4-piperidinyl}-3,4-dihydrocarbostyril (1.6 g) as white powder.

¹H-NMR (CDCl₃) δ ppm: 1.7–2.1 (2H, m), 2.5–3.5 (10H, m), 3.7–4.2 (1H, m), 4.2–4.5 (1H, m), 4.6–5.2 (1H, m), 6.47 (1 H, dt, J=1.2 Hz, J=8.0 Hz), 7.62 (1H, dd, J=1.2 Hz, J=8.0 Hz), 6.95 (1H, dd, J=1.2 Hz, J=8.0 Hz), 7.0–7.3 (7H, m), 7.34 (2H, d, J=8.4 Hz), 7.54 (2H, d, J=8.4 Hz)

EXAMPLE 41

To a solution of 1-{1-[4-(2-imidazolyl)benzoyl]-4-piperidinyl}-3,4-dihydrocarbostyril (1.0 g) and potassium carbonate (0.35 g) in dimethylformamide (10 ml) is added methyl iodide (0.16 ml) under ice-cooling, and the mixture is stirred at room temperature overnight. Further, to the mixture are added methyl iodide (0.16 ml) and potassium carbonate (0.3 g), and the mixture is stirred at room temperature for 8 hours. The mixture is poured into icewater, extracted with ethyl acetate, washed with water and dried over sodium sulfate. After concentrated under reduced pressure, the resulting residue is purified by silica gel column chromatography (eluent; dichloromethane:methanol=25:1) and recrystallized from ethyl acetate to give 1-{1-[4-(1-methyl-2-imidazolyl)benzoyl]-4-piperidinyl}-3,4-dihydrocarbostyril (0.15 g) as colorless scales, m.p. 177°–179° C.

PHARMACOLOGICAL TEST

Experiment 1: V₁ receptor binding assay

Using rat liver plasma membrane preparations prepared according to Ichihara's method [cf: Akira Ichihara, J. Bio. Chem., 258, 9283 (1983)], the plasma membrane (50000dpm, 2×10⁻¹⁰ M) of [H]³-Arg-vasopressin and a test compound (100 ng, 10⁻⁷–10⁻⁴ M) are incubated at 37° C. for 10 minutes in 100 mM Tris-HCl buffer (pH: 8.0, 250 μl) containing 5 mM MgCl₂, 1 mM MEDTA and 0.1% BSA. After incubation, the mixture is filtered three times using the glass filter (GF/F) so as to separate the membrane preparation combined with vasopressin and then washed with the buffer (5 ml). This glass filter is taken out and mixed with liquid scintillation cocktail. The amount of [H]³-vasopressin combined with the membrane is measured by liquid scintillation counter and the rate of the inhibitory effect of the test compound is estimated according to the following equation.

$$\text{Rate of inhibitory effect (\%)} = 100 - \frac{C_1 - B_1}{C_0 - B_1} \times 100$$

$C_1$: The amount of [H]³-vasopressin combined with the membrane in the presence of the test compound (in prescribed amount).
$C_0$: The amount of [H]³-vasopressin combined with the membrane in the absence of the test compound.
$B_1$: The amount of [H]³-vasopressin combined with the membrane in the presence of excess amount of vasopressin (10⁻⁶M).

The results are expressed as IC₅₀ values, which is the concentration of the test compound required to achieve the inhibitory effect in the rate of 50%.

The results are shown in the following Table 2.

TEST COMPOUND 1. 1-[1-{4-[5-(Cyclohexanespiro-4'-(1-piperidinyl))pentyloxy]benzoyl}-4-piperidinyl]-3,4-dihydrocarbostyril
2. 1-{1-[4-(5-Tricyclo[3.3.1.1³·⁷]decanylaminopentyloxy)benzoyl]-4-piperidinyl}-3,4-dihydrocarbostyril hydrochloride
3. 1-{1-[4-(5-Tricyclo[3.3.1.1³·⁷]decanylmethylaminopentyloxy)benzoyl]-4-piperidinyl}-3,4-dihydrocarbostyril
4. 1-[1-{4-[5-(2,2,2-Trifluoroethylamino)-pentyloxy)benzoyl}-4-piperidinyl}-3,4-dihydrocarbostyril
5. 1-[1-{4-[5-[N-Methyl-N-(2-ethoxycarbonylacetyloxyethyl)amino}pentyloxy]benzoyl}-4-piperidinyl]-3,4-dihydrocarbostyril
6. 1-{1-[4-(5-Hydroxy-6-allylaminohexyloxy)benzoyl]-4-piperidinyl}-3,4-dihydrocarbostyril
7. 1-[1-{4-[5-(4-Amino-1-piperidinyl)pentyloxy)benzoyl-}-4-piperidinyl]-3,4-dihydrocarbostyril
8. 1-[1-{4-[5-(4-Trifluoroacetylamino-1-piperidinyl)pentyloxy]benzoyl}-4-piperidinyl]-3,4-dihydrocarbostyril
9. 1-[1-{4-[5-(4-Acetylamino-1-piperidinyl)-pentyloxy)benzoyl}-4-piperidinyl]-3,4-dihydrocarbostyril
10. 1-{1-[4-(5-Methylaminocarbonyloxy-6-diethylaminohexyloxy)benzoyl]-4-piperidinyl}-3,4-dihydrocarbostyril
11. 1-[1-(2-Methoxy-4-ethoxybenzoyl)-4-piperidinyl]-3,4-dihydrothiocarbostyril
12. 1-[1-{4-[5-(1-Pyrrolidinyl)pentylthio]-benzoyl}-4-piperidinyl]-3,4-dihydrocarbostyril
13. 1-{1-[4-(2-Pyridyl)benzoyl]-4-piperidinyl}-3,4-dihydrocarbostyril
14. 1-{1-[4-(2-Imidazolyl)benzoyl]-4-piperidinyl}-3,4-dihydrocarbostyril
15. 1-[1-{4-[2-(2-Aminophenylthio)-1-imidazolyl]-benzoyl}-4-piperidinyl]-3,4-dihydrocarbostyril
16. 1-[1-(2-Methoxy-4-allylthiobenzoyl)-4-piperidinyl]-3,4-dihydrocarbostyril
17. 1-[1-{4-[5-(1-Pyrrolidinyl)pentylsulfinyl)-benzoyl}- 4-piperidinyl]-3,4-dihydrocarbostyril
18. 1-[1-{4-[5-(1-Pyrrolidinyl)pentylsulfonyl]-benzoyl}-4-piperidinyl]-3,4-dihydrocarbostyril
19. 1-{1-[4-(2-Benzimidazolyl)benzoyl]-4-piperidinyl}-3,4-dihydrocarbostyril
20. 1-{1-[4-(2-Phenyl-1-imidazolyl)benzoyl]-4-piperidinyl}-3,4-dihydrocarbostyril 21. 1-[1-{4-[2-(4-Methoxyphenyl)-1-imidazolyl]-benzoyl}-4-piperidinyl]-3,4-dihydrocarbostyril

TABLE 2

| Test Co. No. | IC$_{50}$ ($\mu$M) | Test Co. No. | IC$_{50}$ ($\mu$M) |
|---|---|---|---|
| 1 | 0.047 | 2 | 0.027 |
| 3 | 0.10 | 4 | 0.32 |
| 5 | 0.11 | 6 | 0.14 |
| 7 | 0.028 | 8 | 0.063 |
| 9 | 0.036 | 10 | 0.038 |
| 11 | 0.73 | 12 | 0.034 |
| 13 | 1.2 | 14 | 1.4 |
| 15 | 0.80 | 16 | 0.11 |
| 17 | 3.0 | 18 | 1.9 |
| 19 | 2.1 | 20 | 2.8 |
| 21 | 2.7 | | |

What is claimed is:
1. A carbostyril derivative of the following formula:

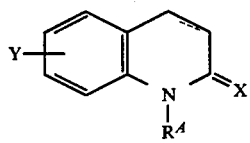

(1)

wherein X is an oxygen atom or a sulfur atom, Y is a hydrogen atom or a lower alkyl, R$^A$ is a group of the formula:

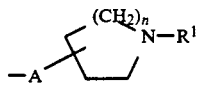

wherein n is 1 or 2, A is a lower alkylene, and R$^1$ is a benzoyl in which the phenyl ring may optionally have one to three substituents selected from a lower alkoxy and an amino having optionally a lower alkyl substituent,
or R$^A$ is a group of the formula:

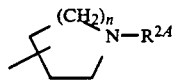

wherein n is as defined above, and R$^{2A}$ is a group of the formula:

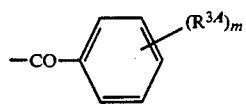

wherein m is an integer of 1 to 3, and R$^{3A}$ is:
i) a lower alkoxy,
ii) a pyridyl, or imidazolyl, which may optionally have a substituent selected from a lower alkyl, an oxo, a phenyl having optionally a substituent selected from a halogen atom and a lower alkoxy on the phenyl ring, and a phenylthio having optionally a substituent selected from nitro and amino,
iii) a lower alkenylthio,
iv) a pyrrolidinyl-substituted lower alkylthio,
v) a pyrrolidinyl-substituted lower alkylsulfinyl,
vi) a pyrrolidinyl-substituted lower alkylsulfonyl,
vii) a group of the formula:

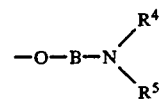

wherein B is a lower alkylene having optionally a hydroxy substituent, R$^4$ is hydrogen atom and R$^5$ is, a tricyclo{3.3.1.1}decanyl, a tricyclo{3.3.1.1}decanyl-lower alkyl, a halogen-substituted lower alkyl, a lower alkoxycarbonyl-lower alkanoyloxy-lower alkyl, a lower alkanoyl, or a lower alkenyl, or R$^4$ or R$^5$ may bind together with the nitrogen atom to which they bond to form a group of the formula:

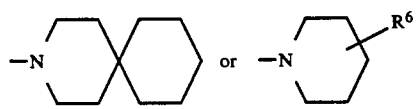

wherein R$^6$ is an amino which may optionally be substituted by a lower alkanoyl having optionally one to three halogen substituents, or
viii) a lower alkoxy having two substituents selected from an aminocarbonyloxy having optionally a lower alkyl substituent and a group of the formula:

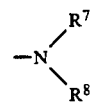

wherein R$^7$ and R$^8$ are the same or different and are each hydrogen atom or a lower alkyl,
and wherein the bond between 3- and 4-positions of the carbostyril ring is single bond or double bond, provided that when all of R$^{3A}$ are lower alkoxy or when R$^5$ is a lower alkanoyl, X is a sulfur atom, and that when R$^5$ is a lower alkenyl and X is an oxygen atom, B is a lower alkylene having a hydroxy substituent, and further that when R$^{3A}$ is a heterocyclic group having a lower alkyl or oxo substituent, the heterocyclic group is bound to the phenyl ring at the position other than the hetero atom, or a salt thereof.

2. A carbostyril derivative of the following formula:

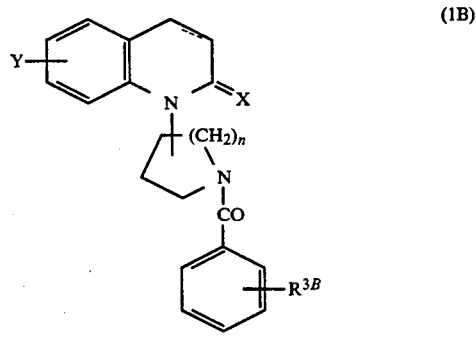

(1B)

wherein X is an oxygen atom or a sulfur atom, Y is a hydrogen atom or a lower alkyl, n is 1 or 2, and the bond between 3- and 4-positions of the carbostyril ring is a single or a double bond, $R^{3B}$ is benzimidazolyl, which may optionally have a substituent selected from a lower alkyl, an oxo, a phenyl having optionally a substituent selected from a halogen atom and a lower alkoxy on the phenyl ring, and a phenylthio having optionally a substituent selected from nitro and amino, or a salt thereof.

3. The compound according to claim 1, wherein X is an oxygen atom, and R is a group of the formula:

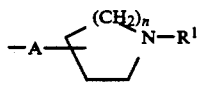

wherein A, n and $R^1$ are as defined in claim 1, or a salt thereof.

4. The compound according to claim 1, wherein X is an oxygen atom, and R is a group of the formula:

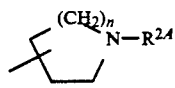

wherein n and $R^{2A}$ are as defined in claim 1, or a salt thereof.

5. The compound according to claim 1, wherein X is a sulfur atom, and R is a group of the formula:

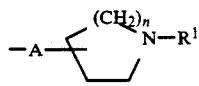

wherein A, n and $R^1$ are as defined in claim 1, or a salt thereof.

6. The compound according to claim 1, wherein X is a sulfur atom, and R is a group of the formula:

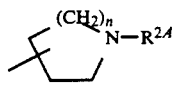

wherein n and $R^{2A}$ are as defined in claim 1, or a salt thereof.

7. The compound according to claim 2, wherein X is an oxygen atom and the bond between 3- and 4-positions of the carbostyril nucleus is a single bond, or a salt thereof.

8. The compound according to claim 2, wherein X is an oxygen atom and the bond between 3- and 4-positions of the carbostyril nucleus is a double bond, or a salt thereof.

9. The compound according to claim 2, wherein X is a sulfur atom, or a salt thereof.

10. The compound according to claim 4, wherein n is 1, or a salt thereof.

11. The compound according to claim 4, wherein n is 2, or a salt thereof.

12. The compound according to claim 7, wherein n is 1, and a salt thereof.

13. The compound according to claim 7, wherein n is 2, or a salt thereof.

14. The compound according to claim 11, wherein $R^{3A}$ is i) a lower alkoxy, ii) pyridyl, or imidazolyl which may optionally have a substituent selected from a lower alkyl, an oxo, a phenyl having optionally a substituent selected from a halogen atom and a lower alkoxy on the phenyl ring, and a phenylthio having optionally a substituent selected from nitro and amino, iii) a lower alkenylthio, or iv) a lower alkoxy having two substituents selected from an aminocarbonyloxy having optionally a lower alkyl substituent and a group of the formula:

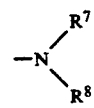

wherein $R^7$ and $R^8$ are as defined in claim 1, or a salt thereof.

15. The compound according to claim 11, wherein $R^{3A}$ is a pyrrolidinyl-substituted lower alkylthio, a pyrrolidinyl-substituted lower alkylsulfinyl, or a pyrrolidinyl-substituted lower alkylsulfonyl, or a salt thereof.

16. The compound according to claim 11, wherein $R^{3A}$ is a group of the formula:

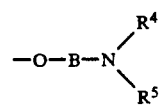

wherein B is a lower alkylene having optionally a hydroxy substituent, $R^4$ is hydrogen atom and $R^5$ is tricyclo{3.3.1.1}decanyl, a tricyclo{3.3.1.1}decanyl-lower alkyl, a halogen-substituted lower alkyl, a lower alkoxycarbonyl-lower alkanoyloxy-lower alkyl, a lower alkanoyl, or a lower alkenyl, or $R^4$ and $R^5$ may bind together with the nitrogen atom to which they bond to form a group of the formula:

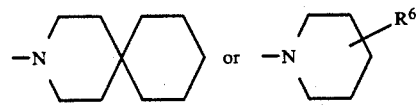

wherein $R^6$ is an amino which may optionally be substituted by a lower alkanoyl having optionally one to three halogen substituents, or a salt thereof.

17. The compound according to claim 13, wherein Y is a hydrogen atom, or a salt thereof.

18. The compound according to claim 13, wherein Y is a lower alkyl, or a salt thereof.

19. The compound according to claim 16, wherein $R^4$ is a hydrogen atom and $R^5$ is tricyclo{3.3.1.1}decanyl, a tricyclo{3.3.1.1}decanyl-lower alkyl, a halogen-substituted lower alkyl, a lower alkoxycarbonyl-lower alkanoyloxy-lower alkyl, a lower alkanoyl, or a lower alkenyl, or a salt thereof.

20. The compound according to claim 16, wherein $R^4$ and $R^5$ may bind together with the nitrogen atom to which they bond to form a group of the formula:

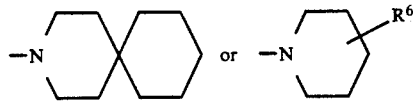

wherein $R^6$ is as defined in claim 16, or a salt thereof.

21. The compound according to any one of claim 14, 15, or 19 wherein Y is a hydrogen atom, and the bond between 3- and 4-positions of the carbostyril nucleus is a single bond, or a salt thereof.

22. The compound according to any one of claim 14, 15, or 19 wherein Y is a lower alkyl and the bond between 3- and 4-positions of the carbostyril nucleus is single bond, or a salt thereof.

23. The compound according to any one of claim 14, 15, or 19, wherein Y is a hydrogen atom and the bond between 3- and 4-positions of the carbostyril nucleus is double bond, and a salt thereof.

24. The compound according to any one of claim 14, 15, or 19, wherein Y is a lower alkyl and the bond between 3- and 4-positions of the carbostyril nucleus is double bond, or a salt thereof.

25. 1-{1-[4-[5-(4-Acetylamino-1-piperidinyl)-pentyloxy]benzoyl]-4-piperidinyl}-3,4-dihydrocarbostyril.

26. 1-{1-[4-(5-Tricyclo[3.3.1.1$^{3,7}$]decanylamino-pentyloxy)benzoyl]-4-piperidinyl}-3,4-dihydrocarbostyril.

27. 1-{1-[4-(5-Hydroxy-6-allylaminohexyloxy)-benzoyl]-4-piperidinyl}-3,4-dihydrocarbostyril.

28. 1-{4-[5-(4-Trifluoroacetylamino-1-piperidinyl)-pentyloxy]benzoyl]-4-piperidinyl}-3,4-dihydrocarbostyril.

29. 1-{1-[4-[5-(1-Pyrrolidinyl)pentylthio]benzoyl]-4-piperidinyl}-3,4-dihydrocarbostyril.

30. A vasopressin antagonistic composition which comprises as an active ingredient a compound of the formula (1) as set forth in claim 1, or a pharmaceutically acceptable salt thereof in admixture with a pharmaceutically acceptable carrier or diluent.

31. A vasopressin antagonistic composition which comprises as an active ingredient a compound of the formula (1B) as set forth in claim 2, or a pharmaceutically acceptable salt thereof in admixture with a pharmaceutically acceptable carrier or diluent.

* * * * *